US012629050B2

(12) United States Patent
Toth et al.

(10) Patent No.: US 12,629,050 B2
(45) Date of Patent: May 19, 2026

(54) METABOLIC AND CARDIOPULMONARY MONITOR

(71) Applicant: LifeLens Technologies, Inc., Ivyland, PA (US)

(72) Inventors: Landy Toth, Doylestown, PA (US); Robert Schwartz, Inver Grove Heights, MN (US); Roy Martin, Maple Grove, MN (US)

(73) Assignee: LifeLens Technologies, Inc., Ivyland, PA (US)

( * ) Notice: Subject to any disclaimer, the term of this patent is extended or adjusted under 35 U.S.C. 154(b) by 99 days.

(21) Appl. No.: 18/503,602

(22) Filed: Nov. 7, 2023

(65) Prior Publication Data

US 2024/0065575 A1    Feb. 29, 2024

Related U.S. Application Data

(60) Division of application No. 16/400,570, filed on May 1, 2019, now Pat. No. 11,844,606, which is a (Continued)

(51) Int. Cl.
*A61B 5/00*        (2006.01)
*A61B 5/08*        (2006.01)
(Continued)

(52) U.S. Cl.
CPC .............. *A61B 5/083* (2013.01); *A61B 5/087* (2013.01); *A61B 5/097* (2013.01); *A61B 5/1135* (2013.01);
(Continued)

(58) Field of Classification Search
None
See application file for complete search history.

(56) References Cited

U.S. PATENT DOCUMENTS

| | | | |
|---|---|---|---|
| 4,198,990 A | 4/1980 | Higgins | |
| 4,871,917 A | 10/1989 | O'Farrell | |
| | (Continued) | | |

FOREIGN PATENT DOCUMENTS

| | | |
|---|---|---|
| EP | 12848306 | 5/2015 |
| WO | PCT/US12/63544 | 2/2013 |

OTHER PUBLICATIONS

Hung Lam et al., "Dual Optical Sensor for Oxygen and Temperature Based on the Combination of Time Domain and Frequency Domain Techniques", Talanta, Mar. 15, 2011, pp. 65-70; 84(1).

*Primary Examiner* — Etsub D Berhanu
(74) *Attorney, Agent, or Firm* — Ryan, Mason & Lewis, LLP

(57) ABSTRACT

A system includes a control unit configured to be worn by a subject including one or more processors operatively coupled to a memory, a wireless transceiver, and a power supply for powering the one or more processors. The system also includes a computing device independent of the control unit including one or more processors operatively coupled to a memory, a wireless transceiver in communication with the wireless transceiver of the control unit, and a display. The system further includes at least one primary sensor and at least one secondary sensor mountable relative to the subject configured to generate respective primary and secondary signals and to communicate the primary and secondary signals to one of the control unit and the computing device.

20 Claims, 11 Drawing Sheets

Related U.S. Application Data continuation of application No. 14/356,083, filed as application No. PCT/US2012/063544 on Nov. 5, 2012, now Pat. No. 10,390,733.

(60) Provisional application No. 61/556,502, filed on Nov. 7, 2011.

(51) Int. Cl.

| | |
|---|---|
| *A61B 5/083* | (2006.01) |
| *A61B 5/087* | (2006.01) |
| *A61B 5/097* | (2006.01) |
| *A61B 5/113* | (2006.01) |
| *A61M 16/00* | (2006.01) |
| *A61M 16/08* | (2006.01) |
| *A61B 5/0205* | (2006.01) |
| *A61B 5/11* | (2006.01) |
| *A61M 16/06* | (2006.01) |
| *A61M 16/10* | (2006.01) |

(52) U.S. Cl.

CPC ............ *A61B 5/6803* (2013.01); *A61B 5/682* (2013.01); *A61B 5/6823* (2013.01); *A61B 5/7282* (2013.01); *A61B 5/742* (2013.01); *A61M 16/021* (2017.08); *A61M 16/085* (2014.02); *A61B 5/02055* (2013.01); *A61B 5/1118* (2013.01); *A61B 5/7415* (2013.01); *A61B 2560/0443* (2013.01); *A61B 2562/0228* (2013.01); *A61B 2562/085* (2013.01); *A61M 2016/0027* (2013.01); *A61M 16/0051* (2013.01); *A61M 16/0672* (2014.02); *A61M 16/0841* (2014.02); *A61M 2016/102* (2013.01); *A61M 2016/1025* (2013.01); *A61M 16/1065* (2014.02); *A61M 2202/0208* (2013.01); *A61M 2205/7536* (2013.01); *A61M 2210/0618* (2013.01); *A61M 2210/0625* (2013.01); *A61M 2230/43* (2013.01)

(56) References Cited

U.S. PATENT DOCUMENTS

| | | | |
|---|---|---|---|
| 6,206,837 | B1 | 3/2001 | Brugnoli |
| 6,468,222 | B1 | 10/2002 | Mault et al. |
| 7,833,480 | B2 | 11/2010 | Blazewicz et al. |
| 2001/0031224 | A1 | 10/2001 | Labuda |
| 2002/0026937 | A1 | 3/2002 | Mault |
| 2002/0029003 | A1 | 3/2002 | Mace |
| 2002/0193698 | A1 | 12/2002 | Moilanen |
| 2003/0023180 | A1 | 1/2003 | Mault |
| 2003/0023181 | A1 | 1/2003 | Mault |
| 2003/0065274 | A1 | 4/2003 | Mault et al. |
| 2003/0208133 | A1 | 11/2003 | Mault |
| 2005/0083527 | A1 | 4/2005 | Flaherty |
| 2005/0177056 | A1 | 8/2005 | Giron et al. |
| 2006/0122528 | A1 | 6/2006 | Gal |
| 2006/0195040 | A1 | 8/2006 | Nason |
| 2007/0106168 | A1 | 5/2007 | O'Neil et al. |
| 2008/0041172 | A1 | 2/2008 | Jaffe |
| 2008/0142019 | A1 | 6/2008 | Lewis et al. |
| 2008/0146890 | A1 | 6/2008 | Le Boeuf et al. |
| 2008/0190436 | A1 | 8/2008 | Jaffe |
| 2008/0319277 | A1 | 12/2008 | Bradley |
| 2009/0151718 | A1 | 6/2009 | Hunter |
| 2009/0281433 | A1 | 11/2009 | Saadat |
| 2010/0186297 | A1 | 7/2010 | Van Duijn |
| 2011/0184297 | A1 | 7/2011 | Vitali |
| 2011/0213271 | A1 | 9/2011 | Telfort |
| 2012/0277612 | A1 | 11/2012 | Li |

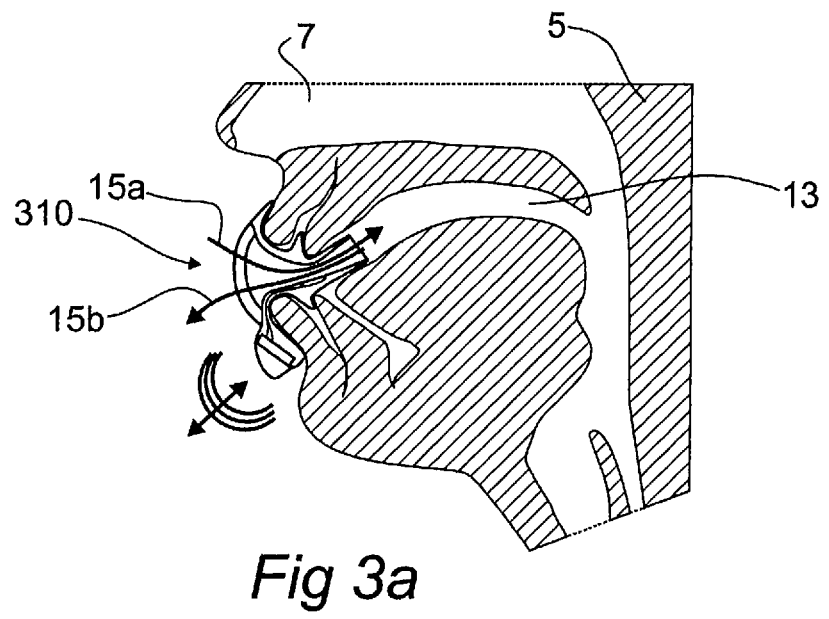
*Fig 3a*
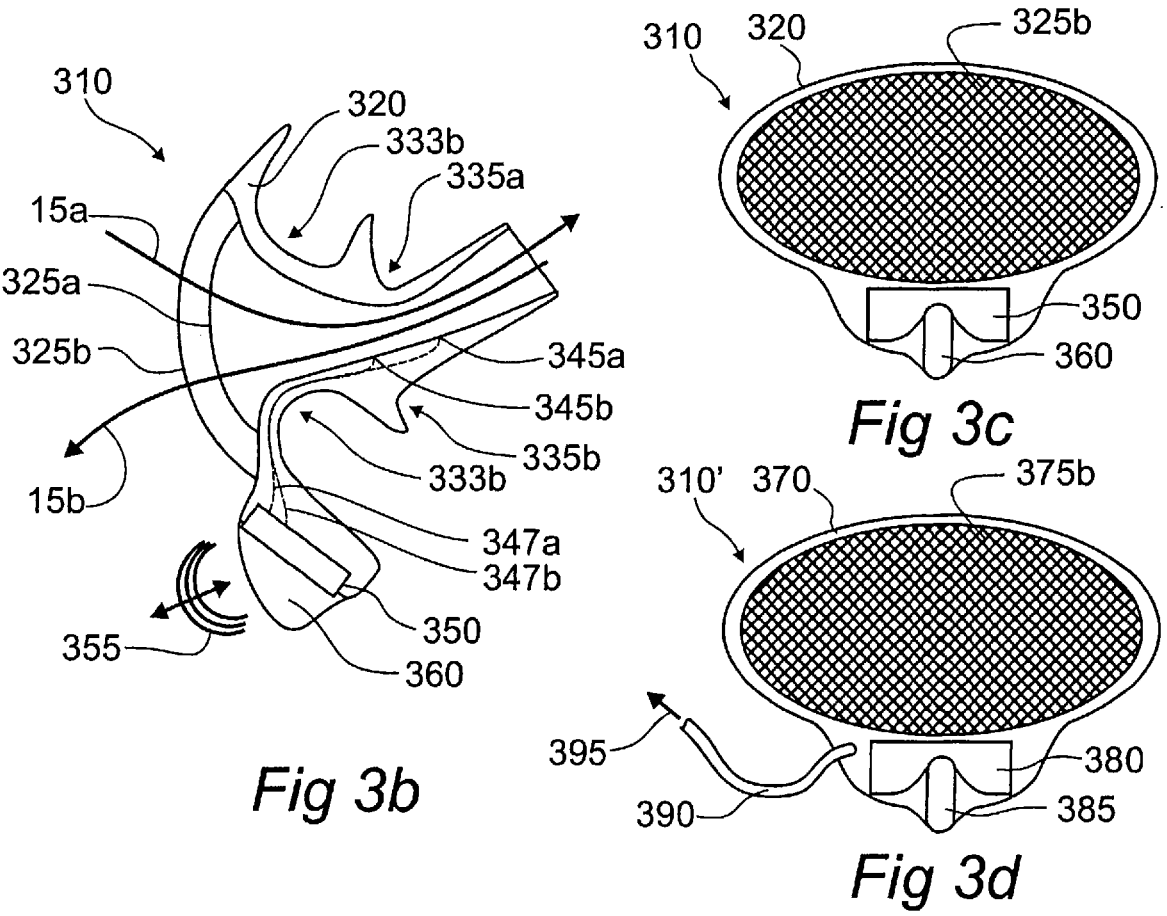
*Fig 3b*
*Fig 3c*
*Fig 3d*

*Fig 14a*
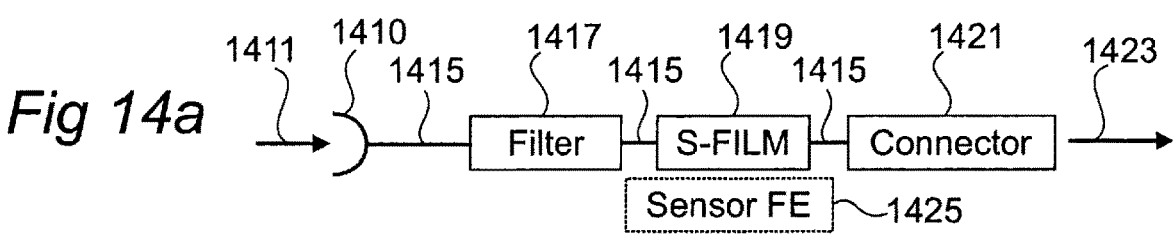
*Fig 14b*
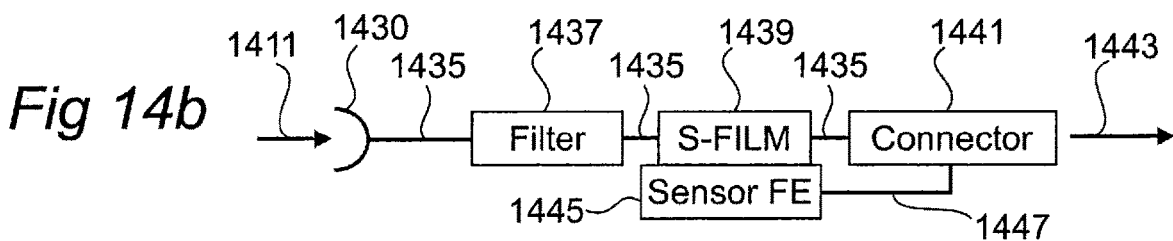
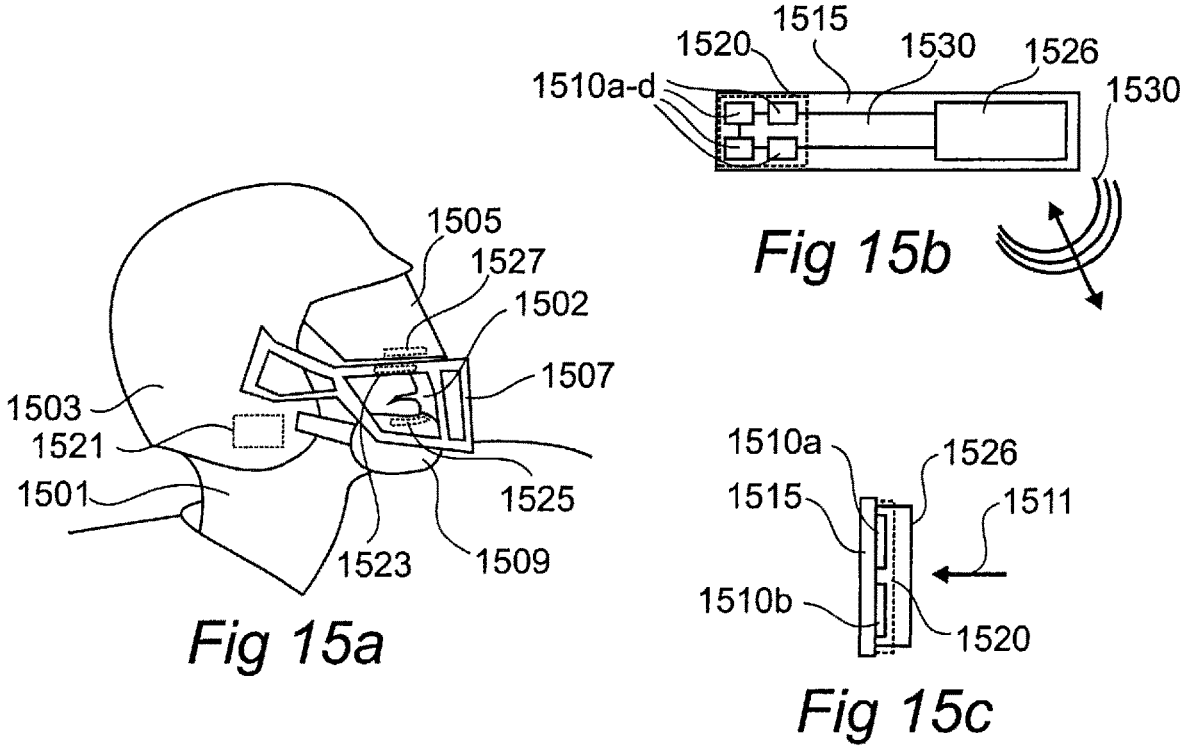
*Fig 15a*
*Fig 15b*
*Fig 15c*

METABOLIC AND CARDIOPULMONARY MONITOR

CROSS-REFERENCE TO RELATED APPLICATIONS

The present application is a divisional of U.S. application Ser. No. 16/400,570 filed on May 1, 2019, which is a continuation of U.S. application Ser. No. 14/356,083 filed on May 2, 2014, which is a national stage application of International Application No. PCT/US2012/063544, filed on Nov. 5, 2012, which claims priority to U.S. Provisional Application Ser. No. 61/556,502, filed Nov. 7, 2011, each of these applications being incorporated in their respective entireties by reference herein.

BACKGROUND

Technical Field

The present disclosure is directed to systems and methods for monitoring and/or assessing metabolic and/or cardiopulmonary parameters of a subject. The disclosure further provides systems and methods for high speed monitoring of metabolic parameters of a subject in a substantially unrestricted setting. The disclosure further provides wearable systems for substantially unobtrusive monitoring of a breath stream from a subject. The disclosure further provides wearable systems for real-time monitoring of the respiratory function of a subject. The disclosure further provides data systems for coordinating simultaneous monitoring of one or more metabolic and/or cardiopulmonary parameters from a plurality of subjects.

Background

The prevalence of obesity in the US exceeds 100 million with approximately 20% of people seeking a medical solution for their condition. Obesity-related burden on US healthcare was $147B in 2008 and continues to increase yearly. Prevalence of obesity related illnesses such as diabetes and congestive heart failure continue to increase. The prevalence of diabetes in the US is greater than 25.8 million adults and children with the cost of care exceeding $200B in 2007. Additionally, over 5.7M Americans suffer from congestive heart failure, which had an estimated healthcare cost of $37.2B in 2008.

A detailed weight loss and fitness program is one essential aspect in the battle against these illnesses. One key factor in controlling weight and fitness is a detailed understanding of a patient's metabolism. A quantitative assessment of metabolism and cardiopulmonary function as they change during the course of an exercise routine, between meals, after taking a dose of a medication, throughout the day, over weeks and/or months provides a wealth of information suitable for assessing patient progress, as well as to assist decision making processes in related therapies. Such information alone or in combination with a medicinal therapy, physical therapy and/or a diet plan can be used to quantitatively track outcomes as well as optimize the therapy to meet the needs of a patient.

Furthermore, in certain respiratory diseases there is a constant overload on or exhaustion of the respiratory system, which often results in respiratory insufficiency, with symptoms including dyspnea and exhaustion. A non-limiting example of such a disease is chronic obstructive pulmonary disease (COPD) or pulmonary emphysema with a distended or flat-standing diaphragm, and/or slack respiratory pathways that tend to collapse. Either a flat-standing diaphragm and/or slack respiratory paths may cause respiratory insufficiency. As a consequence of a flattened, over-extended diaphragm, the patient cannot inhale deeply enough. In addition, the patient cannot exhale sufficiently due to collapsing respiratory paths. This results in an insufficient respiration with an undersupply of oxygen and a rise of carbon dioxide in the blood, i.e., a respiratory insufficiency.

Patients with respiratory insufficiency often require or benefit from supplemental oxygen. However, the supplemental oxygen provided by conventional apparatuses and methods is frequently not adequate to increase ventilation and alleviate symptoms of dyspnea and exhaustion. For example, during periods of light exertion, the patient can become severely dyspneic and exhausted and suffer from elevated $CO_2$ levels, due to the mechanical work associated with breathing which can be eight times more than the normal work required for healthy lungs. Such patients could benefit greatly from real-time monitoring of cardiopulmonary function, both as a means of monitoring progression of their disease, and as an emergency warning system, but also, perhaps as a feedback mechanism to conveniently control a therapy (e.g supplemental supply of oxygen).

Current cardiopulmonary assessment systems are bulky, complex and expensive. This has generally prevented the widespread use of such technologies in the fight against the obesity epidemic and management of chronic disease states outside of the traditional hospital setting. Many such systems require oversight by a skilled professional and may not be suitable for use in unsupervised settings such as the home, office, or gym.

SUMMARY

One objective of this disclosure is to provide a system and method for monitoring metabolic and/or cardiopulmonary parameters of a subject. Another objective is to provide a system and method for discreetly monitoring such parameters in a substantially unconstrained setting. In one aspect, the present disclosure provides a simple, wearable, discreet, self-powered system adapted to monitor metabolic and/or cardiopulmonary parameters of a subject in a substantially unrestricted setting, and communicate such parameters to a user device (e.g. a handheld device, a smartphone, a fitness watch, a media player, gaming console, a biofeedback system, and so forth) and/or an communication system (e.g. a wireless hub, a fitness network, an electronic health record (EHR) network, and so forth). The disclosed system may be worn and utilized by a non-specialist subject in an unconstrained environment while the subject performs a wide range of daily activities.

Another objective is to provide a system and method for monitoring respiratory quotient (RQ) of a subject.

Yet another objective is to provide a system and method for monitoring breath rate (BR), inspiratory duty cycle (IDC), and/or respiratory effort (RE) of a subject in a substantially unconstrained setting.

Yet another objective is to provide a system and method for monitoring calorie expenditure, basal metabolic rate (BMR), resting metabolic rate (RMR), and/or maximum metabolic rate (AMR) of a subject in a substantially unconstrained setting.

Another objective is to provide a system and method for monitoring one or more physiological parameters of a subject including heart rate, respiratory rate, respiratory air velocities and volumes, multi-lead EKG response, hemoglobin saturation, capillary filling, core body temperature, breath temperature, skin turgor, body water content, and the like.

The above objectives are wholly or partially met by devices, systems, and methods according to the appended claims in accordance with the present disclosure. Features and aspects are set forth in the appended claims, in the following description, and in the annexed drawings in accordance with the present disclosure.

In a first aspect there is provided, a wearable system for monitoring metabolic and/or cardiopulmonary parameters of a subject including a control unit adapted to be worn by the subject and configured to analyze a breath gas sample obtained from a breath stream of the subject. The wearable system also includes a sampling module configured to operably communicate the breath gas sample from the breath stream of the subject to the control unit. The control unit is configured to generate one or more signals based on the analysis. The signals are at least partially reflective of at least one metabolic and/or cardiopulmonary parameter of the subject.

The sampling module may include an interfacing component configured to interface with the breath stream of the subject; a connector for detachably connecting the sampling module to the control unit; and at least one lumen configured to provide a fluid communication pathway between the interfacing component and the connector.

The control unit may include a micropump in fluid communication with the sampling module, configured to operably draw the gas sample from the breath stream of the subject. In a non-limiting example, the micropump may be a piezoelectric resonant pump with an operable sound pressure level of less than 40 dB, less than 30 dB, or less than 15 dB.

The sampling module may include one or more sensing membranes arranged so as to operably contact the breath gas sample, the sensing membranes may be configured to generate a response dependent upon one or more properties of the breath gas sample, the control unit may be configured to monitor and analyze the response to generate one or more of the signals.

One or more of the sensing membranes may be arranged along the wall of the lumen.

In aspects, one or more of the sensing membranes may be sensitive to the concentration of a constituent of the breath gas sample selected from the group consisting of oxygen, carbon dioxide, nitrous oxide, nitric oxide, nitric dioxide, carbon monoxide, and water vapor.

In aspects, one or more of the sensing membranes may be sensitive to temperature and/or humidity.

In aspects, one or more of the sensing membranes may include a ruthenium and/or copper complex.

One or more of the sensing membranes may include a transition metal complex and/or a porous crystalline structure including a vapochromic chromophore.

In aspects, one or more of the sensing membranes may have a thickness less than 20 um, less than 10 um, less than 2 um, or the like.

In aspects, one or more of the sensing membranes may include two or more fluorophores, the first fluorophore sensitive to temperature, and one or more of the remaining fluorophores sensitive to one or more constituents of the breath gas sample.

The wearable system may include an emitter and a detector, the emitter configured to operably emit energy towards one or more of the sensing membranes to at least partially elicit the response, the detector configured to operably collect energy emitted from one or more of the sensing membranes to measure the response.

In aspects, the emitter and/or detector may be included in the control unit, arranged in optical communication with one or more of the sensing membranes when the sampling module is operably connected to the control unit.

In aspects, the control unit may include means for controlling the emitter and monitoring the detector to determine if the sampling unit is operably connected to the control unit.

In aspects, the sampling module may include a filter, configured to operably remove contaminants from the breath sample before analysis. In aspects, the filter may include a hydrophobic hollow microfiber array, configured to substantially provide a sterile breath sample for the analysis.

In aspects, the filter may include an optical dye or filler, configured to substantially prevent ambient light from reaching one or more regions of the sampling module.

In aspects, the sampling module may include a boom element, extending from one or more of the lumens comprised within the sampling module, shaped so as to extend from an ear of the subject to a mouth of the subject, configured to interface with the breath stream of the subject.

The interfacing component may include a respiratory flow sensor. The respiratory flow sensor may include an electro-optical sensor for operably measuring a dimensional parameter of an anatomical feature of the subject.

In aspects the wearable system may include a substantially unrestricting respiratory flow sensor, adapted for placement into the breath stream of the subject, configured to operably generate a flow signal related to the breath stream of the subject and communicate the flow signal to the control unit.

In aspects, the respiratory flow sensor may be integrated into the interfacing component.

The interfacing component may be configured for placement within an oral and/or nasal cavity of the subject. In aspects, the interfacing component may include a tooth clip, for attachment to one or more teeth of the subject. In aspects, the interfacing component may include a mouthguard, configured to provide operable retention of the interfacing component within the oral cavity of the subject. In aspects, the interfacing component may include one or more intra nasal constraints, configure to provide operable retention of the interfacing component within the nasal cavity of the subject.

In aspects, the respiratory flow sensor may include a channel, integrated into the mouthguard, the channel operably located in line with the breath stream of the subject. In aspects, the channel may include a flow diffuser, configured so as to operably stabilize flow of the breath stream through the channel.

In aspects, the respiratory flow sensor may be a pneumo-tachometer.

In aspects, the wearable system may include a respiratory volume sensor, adapted for placement onto a chest and/or an abdomen of the subject, configured to operably generate a volumetric signal representative of a respiratory volume of the subject and communicate said volumetric signal to the control unit.

In aspects, the control unit may include a radio and a processor, configured in electrical communication with each other, the radio and processor configured to wirelessly communicate the signal to a user device, a communication system and/or an external coordination device.

In aspects, the control unit may include a power source.

The control unit may include one or more gas sensors arranged in operable fluid communication with the breath gas sample, configured to analyze the breath gas sample. Some non-limiting examples of gas sensors include an electrochemical oxygen sensor, a nondispersive infrared (NDIR) carbon dioxide sensor, a volatile organic compound sensor, a laser spectrometer, a nitric oxide sensor, an acetone sensor, a hydrogen sensor, and the like.

In aspects, the wearable system may further include one or more adjunct sensors, operably arranged in fluid communication with the breath gas sample, configured to analyze the state of the breath gas sample. In aspects, one or more of the adjunct sensors may be selected from the group consisting of a temperature sensor, a humidity sensor, a barometer, and a microphone.

In aspects, the system may include one or more ambient environment sensors, configured to measure one or more environmental parameters associated with an environment surrounding the subject. In aspects, one or more of the ambient environment sensors may be selected from the group consisting of a light sensor, a temperature sensor, a barometer, a humidity sensor, and a microphone.

In aspects, the wearable system may include one or more activity sensors, configured to measure one or more activity parameter associated with a movement of the subject. In aspects, one or more of the activity sensors may be selected from the group consisting of an accelerometer, a gyroscope, an emg sensor, an inclinometer, a GPS, a proximity detector, and a pedometer.

In aspects, the wearable system may include one or more exertion sensors, configured to measure one or more exertion parameter indicative of a level of exertion of the subject. In aspects, one or more of the exertion sensors may be selected from the group consisting of a heart-rate sensor, an ekg sensor, a galvanic skin response sensor, a pulse oximeter, and a core temperature sensor.

In aspects, the sampling module may be disposable.

The wearable system may include an ear bud, configured for placement into the ear of the subject, the ear bud including a speaker in electrical communication with the control unit, the control unit configured to generate an audio feedback signal for delivery to the subject via the ear bud.

In aspects, the ear bud may include one or more ear bud sensors configured in electrical and/or optical communication with the control unit and to monitor a physiological parameter from the subject to form a physiological signal. In aspects, at least one ear bud sensor may be selected from the group consisting of an oximeter, a temperature sensor, bioimpedance and/or biosignal electrodes, a microphone.

In aspects, the control unit may be configured to analyze the physiological signal in combination with the signal.

In accordance with another aspect, there is provided a wearable system for monitoring metabolic and/or cardiopulmonary parameters of a subject including a control unit, with a detector, adapted to be worn by the subject and a sensing membrane, configured to operably interface with a breath stream of the subject and/or a breath gas sample obtained therefrom and to generate a response dependent upon one or more properties of the breath stream and/or the breath gas sample. The detector is configured in optical communication with the sensing membrane to generate a signal dependent upon the response. The signal may be at least partially reflective of one or more metabolic and/or cardiopulmonary parameters of the subject.

The control unit may include an emitter, configured to emit electromagnetic radiation towards the sensing membrane, the response dependent upon the electromagnetic radiation.

In aspects, the sensing membrane may be responsive to the concentration of a constituent of the breath stream and/or the breath gas sample selected from a group consisting of oxygen, carbon dioxide, nitrous oxide, nitric oxide, nitric dioxide, carbon monoxide, and water vapor.

In aspects, the sensing membrane may be responsive to temperature and/or humidity.

The sensing membrane may include a transition metal complex, a ruthenium and/or copper complex, and/or a porous crystalline structure including a vapochromic chromophore.

In aspects, the sensing membrane may have a thickness less than 20 um, less than 10 um, or less than 2 um.

In aspects, the sensing membrane may include two or more fluorophores, the first fluorophore sensitive to temperature, and one or more of the remaining fluorophores sensitive to one or more constituents of the breath gas sample.

The wearable system may include a sampling module configured to operably interface with the breath stream, the sampling module detachably connectable to the control unit, the sensing membrane included in the sampling module. The sampling module may be disposable.

In aspects, the sampling module may include a lumen configured in fluid communication with the breath stream and the control unit. In aspects, the wearable system may include a micro-cannula, the lumen included within the micro-cannula. In aspects, the sensing membrane may be arranged at least partially within the lumen.

In aspects, the control unit may include a micropump configured to draw the breath gas sample from the breath stream of the subject through the lumen.

In aspects, the micropump may be a piezoelectric resonant pump with an operable sound pressure level of less than 40 dB, less than 30 dB, less than 15 dB, or the like.

In aspects, the control unit may include a radio for wirelessly communicating the signal to a user device, a communication system and/or an external coordination device.

The wearable system may include an ear bud, configured for placement into the ear of the subject, the ear bud including a speaker in electrical communication with the control unit, the control unit configured to generate an audio feedback signal for delivery to the subject via the ear bud.

In aspects, the ear bud may include one or more ear bud sensors configured in electrical and/or optical communication with the control unit and to monitor a physiological parameter from the subject to form a physiological signal. In aspects, at least one ear bud sensor may be selected from the group consisting of an oximeter, a temperature sensor, bioimpedance and/or biosignal electrodes, a microphone. In aspects, the control unit may be configured to analyze the physiological signal in combination with the signal.

In accordance with yet another aspect there is provided a wireless flow sensor for use with a wearable system in accordance with the present disclosure. The wireless flow sensor includes a flow channel with a wall, the flow channel adapted for placement within the oral cavity of the subject; a plurality of sampling ports arranged along the wall of the channel; a transducer, in fluid communication with the sampling ports, the transducer configured to generate a flow signal from the pressure difference between two or more of the sampling ports; a power source; and a control circuit, in communication with the transducer and the power source, configured to wirelessly communicate a signal, at least partially derived from the flow signal, to the wearable system.

The wireless flow sensor may include one or more flow diffusing meshes, connected substantially across the channel, the flow diffusing meshes configured to operably diffuse the breath stream of the subject through the channel.

The wireless flow sensor may include a mouthguard, adapted for mounting the wireless flow sensor into the oral cavity of the subject. The channel and the sample ports may be included in the mouthguard.

The wireless flow sensor may include a retention clip, adapted to contact one or more lips and or teeth of the subject, configured to operably retain the wireless flow sensor in the oral cavity of the subject.

In accordance with another aspect, there is provided an external coordination device for use with a wearable system in accordance the present disclosure, including a means for communicating metabolic and/or physiological data from the wearable system to a $3^{rd}$ party service. Some non-limiting examples of a $3^{rd}$ party service include a local network, an electronic health record service, a social network, a fitness data network, a mail transfer agent, a messaging service provider, an emergency call service, and the like.

The external coordination device may include a graphical user interface for communicating metabolic and/or physiological data from the wearable system to a user.

In accordance with another aspect, there is provided a user device for use with a wearable system in accordance with the present disclosure, including a user interface for communicating the metabolic and/or physiological data from the wearable system to a user. The user device may include a processor to generate one or more correlation signals from one or more metabolic and/or cardiopulmonary parameters, one or more activity signals, and/or one or more exertion signals obtained from the wearable system.

In aspects, the user device may be selected from a group consisting of a smartphone, a tablet computer, a laptop computer, a gaming console, a gaming controller, a biofeedback system, a fitness watch, and a handheld computing device.

In aspects, the processor may be configured to generate a biofeedback signal from one or more of the correlation signals, and to display the biofeedback signal to the user.

In accordance with yet another aspect there is provided use of a wearable system in accordance with the present disclosure for monitoring a disease state of a subject. One non-limiting example of a disease state is a chronic obstructive pulmonary disease state. Some other non-limiting examples of disease states include heart failure, metabolic syndrome, diabetes, pulmonary hypertension, and the like.

In accordance with yet another aspect, there is provided use of a wearable system in accordance with the present disclosure in a gaming and/or sporting environment.

In accordance with another aspect, there is provided use of a wearable system in accordance with the present disclosure for monitoring one or more metabolic and/or cardiopulmonary parameters of a subject just prior to, during and after taking a dose of a medication.

In accordance with yet another aspect, there is provided use of a wearable system in accordance with the present disclosure for monitoring a subject in a clinical trial.

In accordance with another aspect, there is provided a method for monitoring metabolic and/or cardiopulmonary parameters of a subject with a wearable system in accordance with the present disclosure, including mounting the control unit onto the subject, interfacing the sampling module with the breath stream of the subject, and powering-on the wearable system. The method may also include connecting the sampling module to the control unit.

In accordance with yet another aspect, there is provided a method for monitoring metabolic and/or cardiopulmonary parameters of a subject with a wearable system in accordance with the present disclosure, including mounting the control unit on the subject, interfacing the sensing membrane with the breath stream of the subject, and powering-on the wearable system.

In accordance with another aspect, there is provided a data system for analyzing metabolic and/or cardiopulmonary parameters of a plurality of subjects, including an external coordination device configured to analyze a dataset, and a plurality of wearable systems each in accordance with the present disclosure. Each wearable system may be configured to monitor the parameters corresponding to one of the subjects and to send one or more signals to the external coordination device, the signals contributing to at least a portion of the dataset.

The external coordination device may be configured to display at least a portion of the analyzed data set and/or metrics generated therefrom for a user.

BRIEF DESCRIPTION OF THE DRAWINGS

Several aspects of the disclosure can be better understood with reference to the following drawings. In the drawings, like reference numerals designate corresponding parts throughout the several views.

FIGS. 3*a-d*—Show aspects of examples of a wireless flow sensor in accordance with the present disclosure.

FIGS. 14*a-b*—Show schematics of examples of a sampling module in accordance with the present disclosure.

FIGS. 15*a-c*—Show examples of a wearable system in accordance with the present disclosure.

DETAILED DESCRIPTION

Figures 1, 2A, 2B, 2C, 2D:
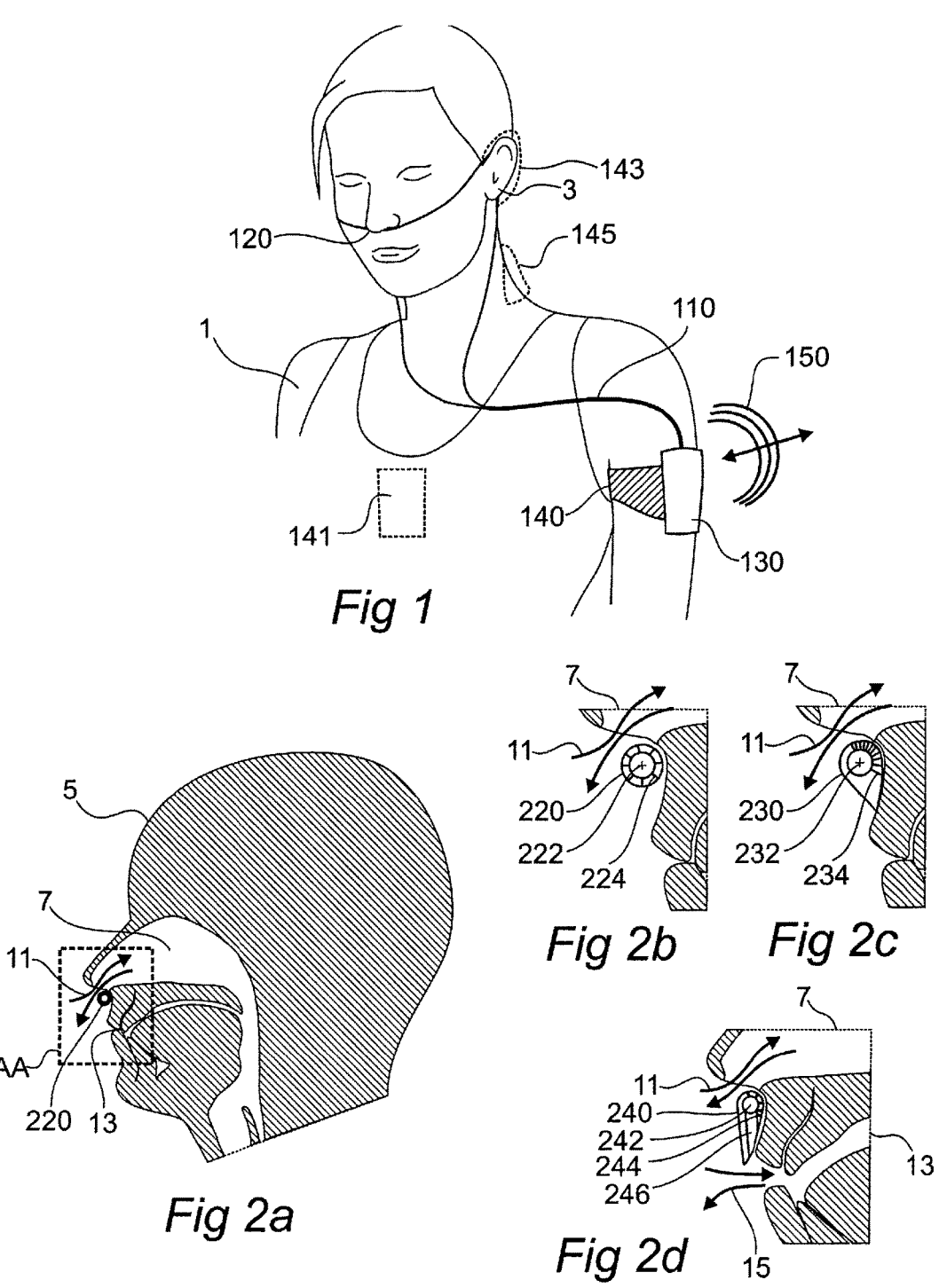
FIG. 1—Shows an example of a wearable system in accordance with the present disclosure.
FIGS. 2*a-d*—Show aspects of examples of a sampling module in accordance with the present disclosure.

Particular embodiments of the present disclosure are described hereinbelow with reference to the accompanying drawings; however, the disclosed embodiments are merely examples of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure. Like reference numerals may refer to similar or identical elements throughout the description of the figures.

One non-limiting illustrative example is a wearable system for monitoring metabolic and/or respiratory parameters of a subject in an unconstrained environment including a control unit for sampling and/or analyzing breath gases from the subject. The wearable system further includes a sampling module for interfacing the control unit with the breath stream of the subject.

By subject is meant a living being (e.g. a human, an infant, a patient, an athlete, a worker, an animal, a mammal, a horse, a dog, etc.).

By unconstrained environment is meant a tether free environment, not being confined to a predetermined space, or necessarily attached to a stationary machine, etc. Such environments include a gym, a fitness center, a lab, a workplace, outdoors, a home, a hospital, a hospice, a clinic, a physiotherapy clinic, a battlefield, a sports facility, a public setting, and the like.

The control unit may include a processor, a power source, a memory element, one or more connectors, a means for generating user feedback, a transceiver, an antenna, one or more gas sensors (e.g. a CO2 sensor, an O2 sensor, an NO sensor, etc.), and/or one or more adjunct sensors (e.g. a humidity sensor, a temperature sensor, a barometer, an accelerometer, etc.).

The control unit may include means for drawing a breath gas sample from the breath stream of the subject, through the sampling module for analysis. In one, non-limiting example, the control unit may include a micropump to provide this function.

The sampling module may include an interfacing component for placement substantially within the nasal and/or oral breath stream of the subject, and a connector for interfacing with the control unit.

The sampling module may take the form of an elongate tube extending from the interfacing component to the connector.

The sampling module and/or the elongate tube included therein may include one or more lumens for fluid communication between the subject and the control unit. Alternatively, additionally or in combination, the sampling module and/or the elongate tube may include one or more electrically conducting wires for electrical communication between the subject and the control unit.

The sampling module and/or the elongate tube may be formed with a multilayered construction. Each layer or a combination of layers may be designed to provide one or more functionalities such as bendability, low gas permeability, optical clarity, a lubricious property, kink resistance, anti-bacterial properties, etc.

The sampling module and/or the control unit may include one or more fluid sensors suitable for assessing the constituents of the fluid exchanged between the subject and the control unit.

The sampling module and/or the control unit may include one or more gas sensors (e.g. an electrochemical oxygen sensor, a chemiluminescent sensor, a nondispersive infrared (NDIR) carbon dioxide sensor, a volatile organic compound sensor, a laser spectrometer, a nitric oxide sensor, an acetone sensor, a hydrogen sensor, etc.) for analyzing the breath gas sample (e.g. the fluid sample). The gas sensor may be arranged so as to form a physical contact with the fluid sample during operation.

The sampling module may include a filter, adapted so as to prevent the exchange of potential bio-contaminants, and/or fluids (e.g. water, saliva, etc.) between the subject and one or more of the fluid sensors. The filter may include one or more hydrophobic membranes or micro-tubular structures and may include a fluid trap, to retain potential contamination within the filter. In one non-limiting example, the filter includes one or more hydrophobic hollow-fiber filtration elements. The hydrophobic hollow-fiber filter elements may be formed from a PTFE material, polypropylene (PP), polyethylene (PE), polysulfone (PS), polyethersulfone (PES), combinations thereof, composites thereof, compounds thereof, and the like. The hollow fiber filter elements may be configured so as to form a fluid trap of sufficient volume so as to retain fluid on the subject side of the filter while provided a clean and optionally sterile gas flow on the analysis side of the filter.

The sampling module may include one or more sensing membranes (e.g. a membrane that elicits a measureable response when placed in physical contact with a breath gas sample). The sampling module may include one or more chemiluminescent gas sensing membranes, one or more temperature sensing membranes, and/or one or more humidity sensing membranes. The sensing membranes may be secured within the sampling module so as to physically contact at least a portion of the fluid passing there-through.

One or more of the membranes may be substantially coated onto the wall of at least one lumen included in the sampling module or attached there-along. The membranes may be placed (e.g. attached, coated, bonded, etc.) adjacently along the length of one or more of the lumens in a pre-determined sequence (e.g. along a lumen wall in a direction extending from the subject towards the control unit—temperature, humidity, oxygen, CO2, temperature).

One or more membranes may be coated so as to have a final thickness of less than 20 um, less than 10 um, less than 2 um. The membranes may be coated so as to contact a passing breath gas sample, while substantially minimizing impact on the flow profile of the passing breath gas sample. A thin sensing membrane may be advantageous for eliciting a fast response to changes in an analyte concentration in the breath gas sample. In aspects, the walls of the membranes may include one or more nanostructured features, configured so as to increase the apparent surface area between the membrane and a fluid passing thereby. Such a configuration may be advantageous for improving response times of the membrane to changes in an analyte in the fluid.

The chemiluminescent gas sensing membrane may include one or more fluorophores such as organic fluorophores (e.g. fluorescent proteins, green fluorescent protein, etc.), lanthanides, transition metal-ligand complexes (e.g. an iridium complex, a ruthenium complex, a platinum complex, a platinum porphyrin unit (e.g. Pt((pentafluorophenyl)porphyrin), tris(4,7-diphenyl-1,10-phenanthroline)ruthenium (II) complex, a copper complex, etc.), and the like. The complex may be bound into a polymer matrix (e.g. chemically linked to, physically entrapped in, etc.), provided as a porous crystalline material, bound to a surface (i.e. of a nanostructured feature), etc. In one non-limiting example, a ruthenium complex may be combined with a polystyrene support to form a sensing membrane with low polydispersity (e.g. a low polydispersity (PDI) star polymer [Ru(2,2'-bipyridine polystyrene (2))(3)](PF(6))(2)). Keeping polydispersity low may be advantageous for improving part to part variability, reducing multiexponential decay effects, extending lifetimes, etc. In another non-limiting example, a crystalline ruthenium complex (e.g. [Ru(1,10-phenanthroline)3][tetrakis(bis-3,5-trifluoromethylphenylborate)]2, etc.) is solution cast onto a carrier (e.g. a glass tubule) and placed within the sampling module. In one non-limiting example, one or more of the sensing membranes may be configured to provide a substantially linear Stern-Volmer quenching response in the presence of sensitive species (e.g. oxygen).

The sensing membrane may include a compound with a UV-VIS-NIR absorbing/emitting solvatochromic and/or vapochromic chromophore (e.g. Cu(xantphos)(phen)+Complexes, [Au2Ag2(C6F5)4L2]n where L is a ligand molecule used to establish sensitivity to particular analytes, etc.) in a loosely packed lattice, embedded in a polymer matrix, etc. The chromophore may experience changes in one or more spectral properties (e.g. absorbance, fluorescence, phosphorescence, etc.) to electromagnetic radiation (e.g. ultra violet, visible and/or infrared radiation) in the presence of the analyte (e.g. ammonia, hydrogen, alcohol, esters, amines, chlorinated organics, organic hydrocarbons, oxygen, carbon dioxide, hydrogen sulfide, etc.) to which it is sensitive. A loosely packed lattice and/or porous matrix or binder may be advantageous for rapid exchange of fluid with the sensing membrane during use. Some non-limiting examples of vapochromic compounds are crystals of copper(I) compounds with sufficient voids for diffusion of gaseous species into the crystal structures. Some non-limiting examples of such compounds include [Cu(POP)(dmp)]tfpb, [Cu(xantphos)(dmp)]tfpb, [Cu(xantphos)(dipp)]tfpb, and [Cu(xantphos)(dipp)]pftpb, where the ligands dmp, dipp, POP and xantphos are given by: POP=bis[2-(diphenylphosphino)phenyl]ether; xantphos=4,5-bis(diphenylphosphino)-9,9-dimethylxanthene; dmp=2,9-dimethyl-1,10-phenanthroline; dipp=2,9-diisopropyl-1,10-phenanthroline (dipp); tfpb=tetrakis(bis-3,5-trifluoromethylphenylborate); and pftpb=tetrakis(pentfluorophenyl)borate. In one non-limiting example, a thin, loosely packed crystalline structure can be formed from the above copper(I) compounds via inkjet printing, solvent casting, self-assembly, and the like of the compound dispersed in a vehicle onto a surface and drying the resulting films, optionally under vacuum conditions. The drying process may be controlled so as to affect the resulting sensitivity of the sensing membrane to the desired analyte.

The chromophores may be, bound into a polymer matrix, a zeolitic lattic, a sol-gel, deposited as a crystalline salt, formed into single or multi-layered porous and/or semi-crystalline nano-film (e.g. via a layer by layer assembly process, sol-gel process, aerogel forming processes, etc.), printed onto a substrate (e.g. a glass retainer, the inner lumen wall of the sensory module, etc.), solvent cast, bound to a porous support structure, etc.

The temperature sensing membrane may include a fluorophore (e.g. N-(1-pyrenylmethyl)-1-pyrenebutanamide, N-(1-pyrenylmethyl)-1-pyreneacetamide, europium(III) β-diketonate complexes, etc.). The fluorophores may be embedded or bound into a polymer network, a hydrogel, poly(vinyl methyl ketone) film, poly(tert-butyl styrene) microparticles, etc. The films may include other analyte sensitive fluorophores, the emission spectrum of which may be different from the temperature sensing fluorophores, thus enabling a dual temperature/analyte sensing membrane. The temperature sensing membranes may be queried using a range of techniques (e.g. fluorescence intensity ratio (FIR), fluorescence lifetime (FL) schemes, etc.).

The humidity sensing membrane may include a moisture sensitive chromophore (e.g. phenolsulfonphthalein) embedded in a polymer matrix such as polymethylmethacrylate. The compound may be added to a vehicle and solution cast onto a substrate (e.g. the wall of a lumen in the sampling module, a substrate, etc.). The film may be placed so as to physically contact a passing breath gas sample when the wearable system is operably interfaced with a subject.

A pH sensing membrane may be based on one or more of several sensing modalities including intramolecular charge transfer, photo-induced electron transfer, excited state intramolecular proton transfer, and the like. In one non-limiting example, a pH sensing membrane may include a 4-amino-1,8-naphthalimide fluorophore and/or a 4-amino-1,8-naphthalimide-containing chromophore.

Dual property sensing membranes may be included (e.g. pH and oxygen sensing membranes, temperature and oxygen sensing membranes, etc.). In such membranes, ratiometric methods may be used to separate one or more property from the complete spectrum emitted from the membrane during use.

The optional polymer binders generally lend support to the sensing membrane and suspend an associated fluorophore or chromophore. Some non-limiting examples of the polymer binder include a rubber, a plastic, a thermoplastic elastomer, poly(2-hydroxyethyl methacrylate)-co-poly(acrylamide), silicon rubbers or gels, polystyrene, cellulose derivatives, poly (styrene-block-vinylpyrrolidine) nanobeads, polytetrafluoroethylene (PTFE), polytrifluoroethylmethacrylate, a sol-gel, and polyurethane-type rubbers and/or hydrogels and the like.

The polymer binder may be designed so as to have high gas permeability (e.g. high oxygen permeability). This may be advantageous in improving the response rate of the gas sensor. The polymer binder may further be modified to improve the gas permeation rate (e.g. made porous, perforated, fibrous, with nanostructured features, etc.). In one, non-limiting example, the polymer binder is a silicone polymer.

The sampling module may include an energy emitter (e.g. a light source, an LED, a heat source, etc.) and a detector (e.g. a photodetector, a thermopile, etc.) oriented to interface with one or more of the sensing membranes included within the sample module. Alternatively, additionally or in combination, the control unit may include an energy emitter (e.g. a light source) and a detector (e.g. a photodetector) oriented to interface with the one or more of the sensing membranes in the sampling module when the sampling module and the control unit are operably connected together. The energy source and detector may interface with one or more of the sensing membranes through the wall of the sampling module, through a portal in the control unit, through a feature on the control unit, etc.

The portal and/or feature may include an optical filtering material to selectively admit or prevent select wavelengths travelling from the exterior of the control unit to reach the detector. In one, non-limiting example wherein the wearable system includes a light source with an emission spectrum in the range of (200-500 nm), and a corresponding sensing membrane that fluoresces with an emission spectrum in the range of (550-800 nm), a suitable optical filtering material may be provided by lithographer's tape (e.g. 3M 616 lithographer's tape provided by the 3M Company, St. Paul, Mn). Suitable optical filtering material may be selected so as to block emitter energy while passing energy emitted from the sensing membrane. Alternatively or in combination, a narrow band detector may be advantageous for separating the fluorescent signal from the emitted signal during use.

The sampling module and/or control unit may include one or more shrouds configured to substantially minimize the amount of ambient light reaching one or more sensing membranes. At least a portion of the sampling module may include an opaque coating, configured to keep ambient light away from one or more of the sensing membranes. The control module may include a latch or panel, suitable for enclosing at least a portion of the sampling module so as to substantially shield one or more sensing membranes from ambient light. Reduction of ambient light near one or more sensing membranes may be advantageous in reducing the noise floor from signals obtained via the membranes, extend the operational lifetime of the membranes, and/or simplification of the sensing circuitry included in the control unit.

The detector may generate one or more signals, related to one or more responses of the sensing membranes to an emitter output in the presence of the breath gas sample. In one non-limiting example, the detector may detect the fluorescence emitted by one or more of the sensing membranes in response to an illumination provided by one or more of the emitters. The fluorescence emitted by the sensing membrane(s) may be measurably affected by the presence of the breath gas sample (due to oxygen quenching, for example). The detector may provide the signal(s) to and/or include a conditioning circuit and/or processor for further processing and generation of a signal related to a metabolic and/or cardiopulmonary parameter of the subject. In some non-limiting examples, the detector may include one or more colorimetric sensors, photodiodes, PIN photodiodes, visible band spectrometers, phototransistors, photomultipliers, integrated optical circuit (IOC) elements, photoresistors, thermopiles, photoconductive camera tubes, charge-coupled imaging devices, and the like.

The control unit and/or sampling module may include a sensory electronics unit for interfacing with one or more sensing membranes. The sensory electronics unit may include one or more emitters, one or more detectors, analog, digital and/or mixed signal conditioning circuits, power management circuits, compensation circuitry, and/or communication circuitry (e.g. I2C, I2S, SPI, units, etc.) in order to operably generate one or more relevant signals from the response of a sensing membrane, the relevant signals being deliverable to one or more elements of the control unit.

In one non-limiting example, the sensory electronics unit includes an emitter, for emitting light towards an associated sensing membrane, and a detector for detecting a fluorescence signal and/or chromatic change in the sensing membrane in response to a passing breath gas sample during use. The sensory electronics unit may further include a driver for substantially minimizing power consumption of the emitter during use, a signal conditioning front end which may include a transimpedance amplifier (optionally bootstrapped, with DC restoration, etc.), an integrating amplifier (e.g. a switched integrating amplifier), charge-sensing ADC, or the like.

In some non-limiting examples, the emitter may include a electroluminescent source (e.g. a light emitting diode [LED], an organic LED [OLED], a quantum dot LED, flexible OLED, a laser diode, a double heterostructure laser, a quantum well laser, a quantum cascade laser, a distributed feedback laser, Vertical-cavity surface-emitting laser [VCSEL], Vertical-external-cavity surface-emitting-laser [VECSEL], external-cavity diode lasers, etc.). The source may emit energy at a wavelength suitable to monitor a property change or elicit fluorescence of a sensing membrane. Some suitable, non-limiting wavebands include infrared, red, green, blue, violet, ultraviolet, etc. In one non-limiting example, the emitter may be a blue emitting InGaN LED and the detector may be a broadband high speed photodiode.

The micropump may be used to draw a fluid sample from the breath stream of the subject, through one or more lumens of the sample module and into physical contact with one or more of the sensing membranes and/or sensors (e.g. gas sensor, adjunct sensor, barometer, flow rate sensor, humidity sensor, etc.).

The micropump maybe an electromagnetic micropump (e.g. an EC-pump, a membrane pump, a rotary valve pump, etc.). Alternatively, a substantially audibly silent micropump may be provided by an electroactive material resonant micropump (e.g. a piezoelectric micropump provided by The Technology Partnership plc. located in Melbourn, UK). An audibly silent micropump may be advantageous in so far as minimizing discomfort of the subject during a long-term monitoring application. The audible noise levels may be quantified using a decibel scale. In a non-limiting example, the piezoelectric resonant pump may operate with a sound pressure level of less than 40 dB, less than 30 dB, or less than 15 dB.

One or more adjunct sensors may be used to monitor the fluid state near the gas sensors and/or sensing membranes (e.g. a barometer, temperature sensor, flow sensor, differential pressure sensor, and/or humidity sensor). The adjunct sensor output may be used to form a compensation signal suitable for improving and/or calibrating the readings from the one or more gas sensors, or sensing membranes, irrespective of environmental variations experienced by the wearable system during use.

The adjunct sensor (e.g. a flow sensor, a differential pressure sensor, etc.) may be used in the control of the flow rate of the breath gas sample through the sampling module. The output of the adjunct sensor may be used by the processor to generate a pump control signal, suitable for adjusting the performance of the micropump. Sensing and optionally controlling the flow rate of the breath gas sample may be advantageous for improving the precision and accuracy of the readings, detecting blockage in sampling module, and the like. Monitoring the flow rate may also be advantageous for substantially minimizing power output to the micropump and so as to maintain an adequate flow rate of the breath sample gas through the sampling module. In some non-limiting examples, the operable flow rate of the breath sample gas may be maintained at substantially about 10-30 mL/s, about 20-40 mL/s, less than 100 mL/s, greater than 2 mL/s.

The micropump may be controlled by a range of control techniques. Some non-limiting examples of control techniques include variable voltage, variable current, pulse width modulated control, adaptive control, etc.

The micropump may be configured to adaptively draw fluid through the sampling module from the subject through the control unit. The micropump may be configured to clear a blockage in the sampling module upon detection. In a non-limiting example, a blockage in the sampling module may be detected by an extra-ordinarily low pressure measured in the breath gas sample near the micropump (e.g. via an adjunct sensor, a barometer, etc.). In this case, the micropump may briefly reverse the flow direction of the breath gas sample so as to clear the blockage from the sample module. Multiple reversals may be used to fully clear the sampling module.

The control unit may include an indicator to alert a user (e.g. a clinician, the subject) as to when the sampling module should be changed. In a non-limiting example, the control unit may monitor pressure levels in the sampling module during use. When the pressure levels drop below a predetermined level, the control unit may trigger an indicator or alert to a user to change the sampling module. The control unit may include an LED indicator, a speaker, an LCD display, etc. so as to provide the alert. An alert may also be provided via a text messaging services, a wireless signal to a user device, etc.

Some non-limiting examples of user devices include a handheld device, a smartphone, a fitness watch, a media player, gaming console, a biofeedback system, and so forth.

The control unit may include a cavity or recess configured to accommodate the sample module when the control unit and the sample module are operably connected. The cavity or recess may be designed to snuggly accommodate the sampling module in order to provide a repeatable and/or predictable orientation between the control unit and the sampling module when in operable connection. An energy source and/or detector positioned within the control unit may be oriented to interface with an operably connected sampling module through the wall of the cavity or recess, and/or a window placed therein.

Such a configuration may be advantageous in coupling reusable control units with disposable sampling modules (e.g. disposable subject interfaces). The disposable sampling module may include one or more sensing membranes and/or films, the properties of which may degrade over time.

The sampling module may include an identification component (e.g. a memory element, a ROM, an RFID chip, etc.) that contains identification markers (e.g. a date stamp, a plant ID, a quality report, configuration information, etc.), and/or calibration information (e.g. calibration parameters, aging parameters, test data, etc.) associated with the sampling module and/or one or more sensors included therein (e.g. a sensor, a sensing membrane, an adjunct sensor, etc.). The control unit may include a system for reading the identification component from the sampling module (such as an RFID reader), such that the identification markers and/or calibration information can be utilized during a monitoring session.

The control unit may include means for detecting the presence of the sampling module. In one non-limiting example, the connector on the sampling module may include a circuit (e.g. an electrical interconnect, a proximity sensor, a magnet, a conducting contact, etc.) while the control unit may include a complimentary circuit (e.g. an electrical interconnect, a detector, a Hall-Effect sensor, an impedance sensor, etc.) for identifying proper connection of the sampling module to the control unit.

In another non-limiting example, the control unit may include a circuit to provide a pulse to one or more of the emitters and a monitoring circuit to monitor an associated detector to determine if the sampling module is presently connected. In this non-limiting example, the detector may output a signal within an expected range when the emitter is pulsed, only if the sampling module is properly connected to the control unit. Otherwise the detector may output an erratic signal. Alternatively, the control unit may provide a succession of pulses to the emitter and monitor the associated detector. If the associated train of samples obtained from the detector has a standard deviation below a predetermined criterion, and the mean sample amplitude is within an expected range, then the sampling module is correctly connected to the controller. Otherwise, the sampling module may not be properly connected and an alert may be sent to a user, etc.

Once the control unit determines that a sampling module is properly connected, a series of diagnostic tests may be performed. The diagnostic tests may be used to calibrate one or more sensors, adjust a sensor offset, determine the drift in a sensor output since it was last used, etc. The control unit may also perform an ambient calibration to compensate for ambient oxygen and carbon dioxide levels, barometric pressure, humidity, and/or temperature that may be present in the local environment surrounding the subject.

The sampling module may be a disposable (e.g. a disposable subject interface). A disposable sampling module may be advantageous to prevent significant bacterial buildup and biofouling of the wearable system, the results of which may not be desirable for the long-term health and integrity of the sensors, the control unit and/or the subject.

The control unit may be provided in a reusable configuration. A reusable control unit may be advantageous for providing monitoring functions at a low cost of delivery.

In one non-limiting example, the walls of the lumens may be formed from a polymer material. Some non-limiting examples include Tygon™, a polyurethane, a multi-layered composite, a thermoplastic elastomer, a polytetrafluoroethylene (PTFE), and the like. In one, non-limiting example, the sampling interface may be at least partially formed from a silicone elastomer. Along the lumen walls, the silicone elastomer may be coated with an alternative polymer, with lower oxygen permeability (such as a polyurethane, or PTFE). In another non-limiting example, silicone portions of a sampling module may be over-molded onto micro-tubules (e.g. one or more polyurethane micro-tubules) that may form the lumens configured to communicate breath gas samples from the subject to the control unit.

In one non-limiting example, one or more of the lumens may be configured with features extending inwards into the lumen so as to prevent collapse of the lumen if it is dramatically bent (e.g. such as during storage and/or use).

The sampling module may include one or more wires for electrically communicating information between sensors and/or sensor elements (e.g. emitters, detectors, etc.) located within the sampling module, sensors located in the interfacing component, and/or an identification component to the control unit. The wiring may be routed through the connector. Alternatively, additionally, or in combination, the wiring may be directed through a second connector that may be attached to the control unit separately from the first connector.

The control unit may include one or more indicators (e.g. an LED, a speaker, a display, etc.) so as to indicate an operational state (e.g. operating, standby, recharging, communicating, etc.), an emergency state (e.g. a blocked sampling module, a replace sampling module indicator, a deficient sampling module, a bad connection, etc.), a data state (e.g. good data, corrupted data, etc.), a physiological state (e.g. an aerobic, an anaerobic state, a state of exertion, etc.), and/or data (e.g. physiological, metabolic, cardiopulmonary, activity, exertion data, etc.), to a user (e.g. the subject, a clinician, a physician, etc.). Alternatively, additionally, or in combination, the control unit may communicate an operational state, an emergency state, a physiological state, a data state, or the like to a communication system, and/or a user device.

Some non-limiting examples of a communication system include a wireless hub, a fitness network, an electronic health record (EHR) network, and so forth.

The wearable system may include one or more feedback mechanisms (e.g. an LED array, a display, a speaker, etc.) to communicate a feedback signal to the user.

In one non-limiting example, the wearable system may include an ear bud speaker, electrically connected to the sampling module. The ear bud speaker may be placed into the ear of the subject during use and may provide feedback to the user during the monitoring process. The wearable system may communicate an audible command to the subject via the ear bud speaker. The audible command may be generated from one or more biofeedback algorithms, and may be related to one or more exercise and/or physiotherapy parameters (e.g. a heart-rate discrepancy, exertion discrepancy, a physiological synch discrepancy, etc.). By discrepancy is meant relating to the difference between a measured parameter and a desired parameter, a previously measured parameter, etc.

The ear bud may include one or more sensors to monitor a physiological parameter from the subject, while providing the alert capability. Some non-limiting examples of ear bud sensors for detecting one or more physiological parameters of the subject include an oximeter, a temperature sensor, bioimpedance and/or biosignal electrodes, a microphone, and the like. In a non-limiting example, the electrical and/or optical communication between the ear bud sensors and a suitable control circuit may be provided via the sampling module and optionally the connector between the sampling module and the control unit.

Alternatively, additionally or in combination, the audible command may be issued by a helper (e.g. a coach, a clinician, a physiotherapist, etc.) intended for the subject. The transmission of the audible command may be enabled via the user device, and/or the communication system and may be wirelessly delivered to the wearable system and provided to the subject via the ear bud speaker. Alternatively, additionally or in combination, the wearable system may include a microphone to provide communication from the subject to the helper, coach, etc.

Alternatively, additionally, or in combination, the control unit may provide an audio stream (e.g. a music playlist, etc.) to the subject via the ear bud speaker during a monitoring session. The audio stream may be provided to the wearable system by a $3^{rd}$ party service (e.g. a music streaming service, via a telecommunication network).

The control unit may include a power source (e.g. a battery, a fuel cell, a solar panel, an energy harvesting device, etc.). In one non-limiting example, the power source is a rechargeable battery (e.g. a rechargeable lithium ion polymer battery). In another non-limiting example, the power source may be a lithium-air battery or optionally a rechargeable lithium air battery.

The control unit may include one or more connectors such as a micro-USB™ connector, to provide a hardwired connection to a host computer, a recharger, or the like.

The control unit may include one or more processors for analyzing signals generated by one or more sensors in the wearable system and/or received from a peripheral or adjunct system (e.g. a wireless ventilation volume sensor, ekg sensor, heart-rate sensor, pulsed oximeter, flow sensor, etc.). The processor may be part of a microcontroller (MC), an application specific integrated circuit (ASIC), a digital signal processor (DSP), a field programmable gate array (FPGA), a system on chip (SoC), or the like. The processor may be configured to analyze the signals, calibrate the signals, compute metabolic and/or cardiopulmonary parameters from the signals, etc. In one non-limiting example, the processor may be configured to accept a breath sample sensor output and an ekg sensor output, potentially corrupted by a respiratory signal. The processor may be configured to use the output from the breath sample sensor to substantially remove the respiratory signal from the ekg sensor output.

The processor may include algorithms for calculating the expected properties of one or more sensing membranes from one or more identification markers, control parameters, lifetime emitter energy calculations (e.g. the emitter power level versus total on time for a given sensing membrane), environmental history data, adjunct sensor data, etc. In one non-limiting example, the processor predicts the properties of a sensing membrane as a function of lifetime emitter energy from a pre-calculated degradation curve (which may be provided as an identification marker, calibration parameter, etc. as part of an identification component included in the sampling module) determined during the design of a sampling module product family, during quality control testing in the manufacture of the sampling module, etc.

The memory element may be configured so as to store data associated with the metabolic and/or cardiopulmonary data, calibration data, timestamps, data associated with one/or more activity signals, exertion signals, environmental signals, etc. The memory element may be embodied on a chip along with the processor, as a stand-alone chip, etc. Some non-limiting examples of memory elements include a flash memory, a static RAM, ferroelectric RAM, magnetoresistive RAM, programmable metallization cells (PMC), phase-change memory (PCM), multi-bit phase-change memory (bmPCM), or the like.

The control unit may include a transceiver, in communication with the processor, configured to wirelessly communicate with a communication system and/or a user device. The transceiver may also communicate with a peripheral and/or an adjunct system (e.g. a wireless flow sensor, ventilation volume sensor, ekg sensor, bioimpedance sensor, heart-rate sensor, pulsed oximeter, flow sensor, etc.). In some non-limiting examples, the transceiver may be configured to communicate in an ISM band (e.g. 13.56 MHz, 433 MHz, 915 MHz, 2.4 GHz, 5.8 GHz, etc.), using a wireless protocol (e.g. Blue Tooth, Blue Tooth low energy, ANT, ANT+, Zigbee, SimpliciTI, Z-wave, proprietary, etc.). The transceiver may be configured as a wireless component (e.g. a host, a device, etc.) in a wireless network based on one or more topologies (e.g. a mesh, a star, a tree, a line, point to point, etc.). In one non-limiting example, the transceiver may be configured as a branch in a tree topology, serving as a host to communicate with a peripheral and/or an adjunct system, while serving as a device (client) to communicate with the user device and/or external coordination system, which may act as hosts in the network.

The control unit may include an antenna, in communication with the transceiver. The antenna may be a wire antenna, a helical antenna, a dipole antenna, a monopole antenna, a PCB trace antenna, a chip antenna, a broadband antenna, a loop antenna, or the like. In one non-limiting example, the antenna is a ¼ wave dipole antenna.

The interfacing component may be placed immediately adjacent to, just outside, or within the nasal and/or oral cavity. Such placement may be advantageous for achieving a reliable breath gas sample from the breath stream of the subject.

In aspects, the interfacing component may include a micro-cannula. The micro-cannula may be configured with one or more micro-holes situated at the entrance to the nasal cavity and/or the oral cavity when operably interfaced with a subject. The micro-holes may be connected to one or more of the lumens included within the sampling module. A plurality of micro-holes may be advantageous in limiting blockages in the interfacing component while operating in the presence of liquids and biofluids (e.g. saliva, mucus, etc.).

In aspects, the micro-cannula may extend into the nasal and/or oral cavity. This may be achieved with one or more features that extend from the main portion of the micro-cannula into the nasal and/or oral cavities. The portion of the micro-cannula operably extending into the oral and/or nasal cavity may include a sensor for measuring and/or estimating the dimensions of the cavity. Such information may be advantageous for use in accurately calculating flow parameters through the oral and/or nasal cavity.

In aspects, the micro-cannula may be formed from thin walled polyurethane, polyethylene, PTFE, etc. The micro-cannula may be formed with multiple lumens, and one or more lumens may be populated with internal protrusions, organized along the wall of the lumens. The internal protrusions may be advantageous in preventing collapse of a lumen during operation and/or storage. In a non-limiting example, the micro-cannula is formed from single lumen substantially transparent polyurethane tubing with an inner diameter of about 0.75 mm and a wall thickness of approximately 0.1 mm.

In aspects, the micro-cannula may be formed with a multilayered construction. Each layer or a combination of layers may be designed to provide one or more functionalities such as bendability, low gas permeability, optical clarity, a lubricious property, kink resistance, anti-bacterial properties, etc. One or more sensing membranes may be deposited along the lumen wall of the micro-cannula so as to operably contact a passing fluid sample. The micro-cannula may include a filter element.

The interfacing component may include a manifold, configured to bridge, with substantially minimal material, both the nasal and oral cavities. Such a manifold may be advantageous to simplify the sampling procedure in some applications. The manifold may include a plurality of sample ports, organized to interface with the nasal and/or oral breath stream. The sample ports may be coupled to one or more lumens in the sampling module.

In one, non-limiting example, the sampling module and the interfacing component have a plurality of lumens. The lumens may be directed to individual breath streams of the subject. A first lumen may be directed towards the left nasal cavity, a second lumen may be directed towards a right nasal cavity, and a third lumen may be directed towards an oral cavity. Each lumen may include one or more sensing membranes (e.g. an oxygen sensing membrane, a carbon dioxide sensing membrane, a humidity sensing membrane, etc.). Breath gas samples may be drawn through each lumen and past the associated membranes. The control unit may analyze the response to each membrane to determine metabolic and/or respiratory parameters from the breath stream passing through each cavity (e.g. left nasal, right nasal, oral). The response from each associated sensing membrane may be used to determine if one or more cavities is blocked or experiencing significantly decreased flow. The response may also be used to generate a nasal/oral feedback signal, suitable for assisting a subject with controlled breathing exercises during a sporting event, a fitness routine, rehabilitation session, a birthing session, etc.

In aspects, the interfacing component may include a boom element, configured to extend from an ear mount on the subject to the mouth of the subject. The boom element may include a shield, a filter and a lumen for delivering a breath gas sample through the sampling module. The shield may be configured to protect the lumen from wind gusts, etc. in the ambient environment around the subject. The filter may include a biocontaminant filter (e.g. a micro-porous polymer membrane to keep fluids, saliva, etc. from entering the lumen) as well as optionally, an optical filter (e.g. a dye to keep ambient light from entering the lumen). The interfacing component may include one or more sensing membranes suitable for monitoring one or more parameters of the breath stream.

The interfacing component may be adapted for placement partially, mostly, or completely within the oral cavity of the subject, via inclusion of a mouthguard, bite clip, tooth clip, retainer, helical nasal retainer, etc.

In aspects, the interfacing component may include a mouthguard (e.g. an upper teeth guard, a lower teeth guard, a full mouth guard, etc.). The mouthguard may be fashioned with one or more sample ports, the sample ports connected to one or more lumens within the sampling module. The sample ports may be arranged towards the front of the mouthguard (towards the lips of the subject during a monitoring session) so as to substantially minimize exposure to saliva. The sample ports may be covered with a hydrophobic perforated cover (e.g. a hydrophobic mesh), suitable for substantially minimizing fluid ingress into the sample ports during operation.

In aspects, the interfacing component may be fashioned as a tooth clip (e.g. for attachment to one or more teeth within an oral cavity). The tooth clip may include a wire clip, configured to bridge and conform to one or more teeth, and a padded sampling region, adapted to sample breath gases from the oral breath stream of the subject. The padded sampling region may be connected in fluid communication with one or more lumens in the sampling module. Such a configuration may be advantageous for monitoring one or more parameters in a substantially unrestricted manner, over a potentially prolonged period of time.

In aspects, the interfacing component may include one or more channels, configured to be placed substantially within the breath stream of the subject. The channels may form a conduit of known dimensions through which the breath stream may pass during a monitoring session. The known dimensions of the conduit may be advantageous for improving stability and repeatability of the flow profile near one or more sample ports and/or flow sensors. The channel may include one or more diffusers and/or partial obstructions, arranged across the channel such that the breath stream must pass through the diffuser during use. The diffuser may include a filter element, to remove biocontaminants from the breath stream, and/or a flow adjuster, suitable for forming a stabilized flow stream from the breath stream. In aspects, the diffuser may include a flow adjuster, formed from a polymer mesh, suitable for altering the flow stream in the vicinity of the channel and optionally for forming a measureable pressure drop across sample ports during a non-zero flow rate in a breath stream (during use).

The interfacing component may include two or more ports suitable for sampling the pressure variation along the breath stream of the subject. The ports may be placed such that they lay along the trajectory of the breath stream of the subject during use. The ports may be connected in fluid communication to one or more pressure transducers. The pressure transducer may be arranged to generate a flow pressure signal related to the difference(s) in pressure between one or more surfaces of the transducer. The flow pressure signal as provided by the pressure transducer may be used to determine flow rate through the interfacing component. The ports may communicate with the pressure transducer via a plurality of the lumens included in the sampling module. In aspects, the interfacing component may include a flow channel with a plurality of ports, the ports connected to a pressure transducer, and the pressure transducer configured to generate a flow pressure signal during use. The flow pressure signal may be computationally combined with calibration parameters (e.g. as determined during the design, or quality testing of the interfacing component) to determine the flow rate of the breath stream through the channel. In one non-limiting example, the interfacing component includes two ports and the flow rate is determining using a pneumotachometer.

In aspects, the interfacing component may include a MEMs thermal mass flow (TMF) sensor (e.g. a half-bridge sensor, a full bridge sensor, with integrated ambient temperature sensor, etc.), oriented within and/or in fluid communication with the breath stream. The TMF sensor may provide a signal related to the breath stream of the subject. Sensory signals from one or more adjunct sensors may be used to calibrate and/or otherwise improve the output of the TMF sensor to achieve a more accurate flow rate reading from the breath stream.

The connector in the sampling module may include a twist locking interface (e.g. a Leur interface), a push connector, or the like for interfacing with the control unit. The connector may include a seal (e.g. a rubberized seal) so as to maintain a substantially air tight interconnection with the control unit when operably connected. The connector may include fluid communication means and/or electrical communication means to operably convey fluids and/or signals with the control unit.

The sampling module may include a nasal and/or oral packet, loaded with a bolus of a medicament and/or chemical for release into the respiratory system of the subject. The wearable system may monitor metabolic and/or cardiopulmonary response of the subject to the bolus. The wearable system may generate a warning dependent on the physiological response of the subject to the bolus. The wearable system may generate a treatment completed signal, indicating that sufficient medicament has been delivered to the subject. The system may include means for monitoring flow parameters of the breath stream of the subject in the vicinity to the bolus to ensure proper dynamics for delivery of the dosage during inhalation thereof by the subject. Additionally, alternatively, or in combination, the sampling module may include a bolus sensor, such as a gas sampling port, to determine the state of the bolus as it is up taken by the subject. In one non-limiting example, the wearable system may indicate to the subject when at least a portion of the bolus is still present and/or when the bolus has been substantially up taken by the subject.

The control unit may be configured so as to be worn on the body of the subject (e.g. on the arm, belt, belt holster, neck, behind the ear, in a pocket, as at least a portion of a bandage, as at least a portion of an adhesive patch, etc.). The control unit may also be adapted for mounting on equipment in the vicinity of the subject (e.g. a bicycle, an exercise machine, a treadmill, etc.). In one non-limiting example, the control unit configured to be mounted in a pocket, the pocket attached to an armband. The armband may be worn by the subject during a monitoring session. In another non-limiting example, the control unit is integrated into an ear clip, configured to be worn behind the ear of the subject during a monitoring session. The control unit may be considerably small in weight and profile. In aspects, the control unit may weigh less than 75 grams, 50 grams, 35 grams, the control unit may have a characteristic dimension (e.g. a thickness) of less than 15 mm, less than 10 mm, less than 7.5 mm.

The wearable system may include one or more adjunct sensors (e.g. a temperature sensor, a humidity sensor, a barometer, and a microphone), operably arranged in fluid communication with the breath gas sample and configured to analyze an aspect or property of the breath gas sample. The adjunct sensors may be located in the control unit, sampling module or otherwise mounted on the subject. The adjunct sensors may provide information suitable for calibrating readings irrespective of the environment in which the subject is monitored.

The wearable system may include one or more ambient environment sensors (e.g. a light sensor, a temperature sensor, a barometer, a humidity sensor, a microphone, or the like), configured to measure one or more environmental parameters associated with an environment surrounding the subject. The ambient sensors may be used in conjunction with one or more sensing membranes and/or adjunct sensors to convert and/or calibrate a metabolic and/or cardiopulmonary parameter to a standard reading state. Such information may be advantageous when monitoring a subject in an unconstrained environment.

The wearable system may include one or more activity sensors (e.g. an accelerometer, an emg sensor, an inclinometer, a gyroscope, a GPS, a proximity detector, a cadence sensor, and a pedometer), configured to measure one or more activity parameters associated with a movement of the subject. The activity sensors may be included in the control unit, the sampling module or otherwise attached to the subject. The activity sensors may be advantageous for monitoring movements of the subject, generating usage reports, and the like. Activity sensors may also be advantageous for use in emergency monitoring of the subject, to determine the state and positioning of the subject in case of a problem, etc. In one non-limiting example, signals derived from one or more of the activity sensors may be used by one or more algorithms to at least partially remove motion artifacts from the metabolic and/or cardiopulmonary parameters.

The wearable system may include means for providing one or more correlation signals generated by comparing an activity signal (e.g. a gait signal generated from one or more pedometers, accelerometers, etc.), an exertion signal (e.g. a heart rate, cardiac ejection, oxygen saturation, etc.) and/or a cardiopulmonary parameter (e.g. respiratory cycle, lung volume change, heartbeat, etc.) for providing feedback to the subject. The correlation signal may be provided to the subject or compared with a desired value for the purpose of synchronizing or correlating (e.g. synchronously but with a delay and/or phase shift) one or more activities, exertions, and/or cardiopulmonary parameters. For correlation, the delay may be fixed, variable or real-time programmable. In one, non-limiting example, the wearable system may generate a correlation signal by timing the cadence of feet hitting the ground while a subject is running in combination with a simultaneously obtained cardiac ejection signal. The correlation signal may be presented to the subject in the form of an audible tone (e.g. with varying pitch, timber, etc.

related to the correlation signal), an audible cue (e.g. "step . . . step . . . "), a visual cue (e.g. a blinking LED, etc.) so as to provide the user with the opportunity to adjust the correlation signal (e.g. so as to synchronize the events, de-synchronize the events, etc.). The correlation signal may also be used to inhibit synchronization of events (e.g. to de-synchronize physiology events with the mechanical events of physical activity). Such de-synchronization may be advantageous for minimizing organ damage during a training session.

In another non-limiting example, signals derived from one or more of the activity sensors may be used to construct a gait signal. The gait signal may be compared with the respiratory signal (e.g. as obtained from one or more gas sensors, sensing membranes, flow sensor, and/or a respiratory volume signal), to construct a gait-respiratory synchronization signal. The gait-respiratory synchronization signal may be provided to a user (e.g. a coach, a clinician, the subject) as a biofeedback signal. Alternatively, additionally or in combination, the gait-respiratory synchronization signal may be operably used by the processor to construct a biocorrection signal. The biocorrection signal may be a measure of the dis-connection between the gait and respiration of the subject. The biocorrection signal may be used to drive one or more feedback and/or alert means on the control unit, to assist the user and/or the subject directly in synchronizing the gait and the respiration rate of the subject during a monitoring session, to assist in de-synchronizing the gait and respiration rate, or the like.

The wearable system may include one or more exertion sensors (e.g. a heart-rate sensor, an ekg and/or emg sensor, a galvanic skin response sensor, a pulse oximeter, a core temperature sensor, a cardiac output sensor, a respiratory volume sensor, etc.), configured to measure one or more exertion parameter indicative of a level of exertion of the subject. The exertion sensors maybe reflective of a change in metabolic state, which, although qualitative, may be advantageous in correlating metabolic and/or cardiopulmonary parameters with other bodily functions, such as heart exertion, muscle exertion, etc.

In aspects, one or more exertion sensors may be used to produce an exertion signal. The exertion signal may be combined with one or more metabolic and/or cardiovascular parameters to classify a metabolic rate (e.g. a basal rate, an active rate, a peak rate, etc.), or to generate a performance parameter (e.g. VO2max, a recovery rate, an efficiency parameter, etc.).

The wearable system may include a nasal plug or clip, configured so as to limit the breath stream of the subject from passing through the nasal cavity during a monitoring session. The nasal plug or clip may be advantageous in obtaining an accurate metabolic parameter during a resting condition (e.g. a subject state of minimal exertion) while monitoring only the oral breath stream of the subject.

The wearable system may be integrated with a supplemental oxygen delivery system, as used in the treatment of various respiratory diseases. The oxygen delivery cannula may be integrated into the sampling module, or vice versa. The control unit may be integrated into the oxygen supply delivery system, or mounted upon the oxygen supply line. Signals generated by the wearable system may be used to assess the effectiveness of oxygen delivery to a subject; to recommend adjustments to a user regarding the level of oxygen delivery; used as control feedback signals to automatically adjust oxygen delivery levels so as to provide an optimized and/or personalized therapy for a subject; or the like. The wearable system may be configured to calculate subject diagnostic information such as changes in ventilation volume over time, changes in heart-rate compared with an activity parameter, etc.

Another illustrative example is a respiratory volume sensor (RVS) configured to monitor the volume of the chest cavity so as to monitor the volume of air exchanged with the lungs in real-time. The respiratory volume sensor may include a plurality of bands and/or motion sensors adapted for placement on the chest and/or abdomen of the subject. In one, non-limiting example, the respiratory volume sensor includes two strain gauge bands, the first band adapted for placement around the chest of a subject and the second band adapted for placement around the abdomen of the subject. The respiratory volume sensor may be integrated into a piece of clothing (e.g. a cumber bun, a girdle, a shirt, etc.)

The bands may include soft, elastic, strain indicating films so as to operably measure the circumference of the chest and/or abdomen of the subject in real-time. In aspects, circumference changes of the chest and abdomen may be combined to determine the changes in the lung volume of the subject during breathing. Respiratory air flow rates may be determined from the time derivative of the lung volume measurements.

The respiratory volume sensor (RVS) may include a circumference and/or impedance sensing element, sensory electronics (e.g. RVS sensory electronics), a processor (e.g. a RVS processor), a memory element (e.g. a RVS memory element), a radio, and/or a power source.

In aspects, the circumference sensing element may include a strain indicating film. In one, non-limiting example, the strain indicating film may be formed form an elastomeric element sandwiched between electrode elements. The elastomeric element may be fabricated with a thickness that varies along its length, so as to form a rippled structure. The rippled structure may extend the apparent strain that can be achieved in the elastomeric element, while limiting actual strains at the surface of the element. The electrode elements may be formed from thin film metallic materials, electrically conducting polymer composites, inks, gels, or the like. The elastomeric element may change electrical properties (e.g. capacitance) with changes in length (e.g. changes in circumference of the chest and/or abdomen of the subject). Thus such a strain indicating elastomeric film may provide an electrically measureable property that varies in response to changes in the lung volume of the subject.

Alternatively, additionally, or in combination, the circumference sensing element may include an inductive coil strain gauge. The inductive coil strain gauge includes an electrically conducting coil, optionally wound around an elastomeric core (e.g. a polyurethane, resilin, thermoplastic elastomer, silicone, polybutylene rubber, etc.). The elastomeric core may include one or more ferromagnetic filler materials suitable for increasing the overall inductance of the electrically conducting coil. The electrical properties (e.g. inductance) of the coil may change with length (e.g. circumference of the chest and/or abdomen of the subject). Thus such an inductive coil strain gauge may provide an electrically measureable property that varies in response to changes in the lung volume of the subject.

The RVS processor may be configured to communicate with a wearable system in accordance with the present disclosure, via the RVS radio. The RVS processor may be configured to analyze and compress data relating to the respiratory volume of the subject. The RVS processor may also generate one or more respiratory characteristics (e.g. a phase component, an amplitude component, a timing element, etc.) for communication with the control unit, a user device and/or a communication system. The RVS processor may include means for compressing signals, conditioning signals (e.g. filtering), and the like so as to substantially minimize the amount of data communicated between devices and/or provide higher quality signals for communication between devices.

The respiratory volume sensor may include a memory element for storing respiratory volume data, associated parameters, calibration data, identification information, etc. Some non-limiting examples of suitable memory elements include a flash memory, a static RAM, ferroelectric RAM, magnetoresistive RAM, programmable metallization cells (PMC), phase-change memory (PCM), multi-bit phase-change memory (bmPCM), or the like.

The RVS sensory electronics may include analog, digital and/or mixed signal conditioning circuits, power management circuits, compensation circuitry, communication circuitry, etc. in order to operably generate one or more relevant signals for delivery to the RVS processor.

In yet another illustrative example, a wireless flow sensor is configured to quantitatively assess the flow rate of the breath stream from a subject. The wireless flow sensor includes a manifold, configured to be substantially placed within the oral cavity of a subject, one or more transducers, in fluid communication with the breath stream via the manifold, configured to operably generate one or more signals related to the flow of the breath stream in the vicinity of the manifold, and a control circuit, suitable for monitoring one or more of the signals and communicating (e.g. wirelessly communicating) the flow rate information to a wearable system in accordance with the present disclosure, a user device, and/or a communication system.

The manifold may further include one or more channels and one or more sample ports, the sample ports configured to operably interface with the breath stream of the subject and the channels configured to provide fluid communication between the sample ports and the transducers. In one non-limiting example, the sample ports are arranged with roughly equidistant spacing along the length of the manifold.

The manifold may include a conduit configured such that the breath stream of the subject substantially passes through the conduit during a monitoring session. The conduit may include one or more diffusers and/or partial obstructions, attached to the conduit such that the breath stream of the subject substantially passes through the diffusers or partial obstructions during use. The diffuser(s) may be advantageous for reducing large turbulent disruptions in the breath stream of the subject during a monitoring session.

Another illustrative example is a user device and/or a communication system configured to communicate with a wearable system in accordance with the present disclosure. The user device may be a smartphone, a tablet computer, a handheld computing device, a host laptop, a fitness watch, a gaming console, a gaming controller, a biofeedback system, or the like. The communication system may be a wireless hub, a server, a fitness network, a cellular network, or the like.

The user device and/or communication system may be suitable for interfacing with a user (e.g. the subject, a clinician, a patient, a physician, a technician, a physical trainer, a clinical trial coordinator, etc.) and/or a machine (e.g. a server, an electronic health record system, a database, a clinical trial database, etc.). The user device and/or communication system may include a graphical user interface, an alarm system, a touch interface, or the like, by which a user and/or machine may assess the data (e.g. metabolic and/or cardiopulmonary data, activity data, etc.), interface with and/or manipulate the data, and/or configure one or more devices (e.g. the lung volume sensor, the wireless flow sensor, the control unit, etc.), aggregate data from a subject population, etc.

In yet another illustrative example a data system is configured to monitor metabolic, activity, exertion, and/or cardiopulmonary parameters simultaneously from a range of subjects. The data system includes an external coordinating device (e.g. a user device, a communication system, etc.) for communication with one or more wearable systems in accordance with the present disclosure, for monitoring metabolic and/or cardiopulmonary parameters of one or more subjects. The external coordinating device is configured to aggregate data from the plurality of wearable systems, each of the wearable systems operably connected with an associated subject.

The external coordinating device may aggregate the metabolic, cardiopulmonary, activity, exertion, environmental, adjunct, and/or calibration data obtained from one or more wearable systems, relating to one or more associated subjects, with extended subject data (e.g. personal data, physical data, health history, previous metabolic and/or cardiopulmonary data, lab results, medication dosage, etc.) as stored locally on the external coordinating device or provided by a $3^{rd}$ party service (e.g. an electronic health record service, a clinical trial database, a social network, a local database, a fitness data network, a mail transfer agent, a messaging service provider, an emergency call service, a cloud data system, etc.). The external coordinating device may exchange data with the $3^{rd}$ party system for purposes of storage, analysis, report construction, etc.

The data system may be advantageous for use in a sporting environment, a training environment, a hospice, to monitor subjects enrolled in a clinical trial, etc. where several subjects are under analysis at any given time. In one, non-limiting example, the data system may be used in a sporting environment (e.g. during a hockey game). In this example, each player on a team may constitute a subject, and may be monitored with an associated wearable system. A user device, included in the data system may be used by a coach to track the performance, gas-tank, exertion parameters, etc. of each player during the game. The user device may suggest substitutions to a coach based on the present state of any given player in the game, may display the performance of a player versus training metrics, predict the energy reserve that a player may have remaining, etc.

The user device and/or external coordination device or the data system may exchange data between the wearable monitoring system and the $3^{rd}$ party service. The external coordination device may aggregate data from the monitoring system and the $3^{rd}$ party service to display and/or highlight key information and/or data relationships for the user. The external coordination device may push monitored data (e.g. metabolic, cardiopulmonary, activity, exertion, emergency data, etc.) to the $3^{rd}$ party service.

In one, non-limiting example, the $3^{rd}$ party service is a social network (e.g. Facebook™ Google+™, Patients like me, Gyminee™, Fitizens™, FitLink™, Nikeplus™, etc.). In this example, the external coordination device may provide or receive data relating to the subject to the $3^{rd}$ party service. Such data may include metabolic data, cardiovascular data, progression of a disease state, data trends taken over a time period (e.g. over a workout session, over a day, a week, a month, since a previous office visit, etc.), achievements (e.g.

improvements in performance, metabolic parameters, reached goals, etc.), and the like.

In another, non-limiting example, the $3^{rd}$ party service is a messaging service provider (e.g. a provider for sending text messages such as short message services (SMS), ANSI CDMA networks, Digital AMPS, satellite, landline networks, multimedia messaging services (MMS), etc.). In this example, the external coordination device may provide data to or receive data from the $3^{rd}$ party service. Such data may include alerts, emergency calls, reports, data requests, and the like.

In aspects, the user device and/or external coordination system may coordinate several wearable systems so as to simultaneously monitor a plurality of subjects. Data from each wearable system may be aggregated for presentation to a user (e.g. a coach, a physical trainer, a fitness teacher, a patient monitoring datacenter, etc.) so as to present metrics related to one or more subjects during the monitoring session. This configuration may be advantageous in a sporting environment, such as a hockey game, for a coach to assess performance of players, compare present physical output to previously stored metrics, assess remaining energy tanks in players (based on previous assessments, training metrics, etc.), and the like.

Another illustrative example is a method for monitoring one or more metabolic and/or physiological parameters of a subject using a wearable system in accordance with the present disclosure. The method includes attaching the control unit onto the subject, interfacing the sampling module with the breath stream of the subject, and powering on the wearable system.

The method may also include connecting the sampling module to the control unit, calculating a metabolic parameter, diagnosing a disease state, etc.

Yet another illustrative example is the use of a wearable system in accordance with the present disclosure, to monitor a disease state of a subject.

The wearable system may be used to monitor a range of disease states of the subject, non-limiting examples include congestive heart failure, respiratory diseases (e.g. chronic obstructive pulmonary disease [COPD], emphysema, asthma, sleep apnea, etc.), metabolic diseases (e.g. metabolic syndrome, pre-diabetes and/or Type I or Type II diabetes mellitus, etc.), metabolic events, (glucose events and proportionality, ketones in the breath, onset of ketoacidosis, etc.), and the like.

In one, non-limiting example, a wearable system in accordance with the present disclosure may be integrated into a supplemental oxygen delivery system intended for use with a subject suffering from chronic obstructive pulmonary disease (COPD). The wearable system may be configured to monitor oxygen delivery to the oral and/or nasal cavity of the subject as well as monitor the exhaust breath gases from the subject. Such information may be used to determine if the subject is receiving sufficient oxygen, may be used to assess emergency situations that may arise with the subject (e.g. severe dyspneic response, collapse, etc.). The wearable system may also monitor and track the overall progression of COPD in the subject. Such tracking may be advantageous for changing long-term therapies for the subject, comparing the efficacy and/or compliance of therapies across a population of subjects, tracking therapeutic outcomes, updating a care physician on the state of a patient, etc.

Another illustrative example is the use of a wearable system, in accordance with the present disclosure, in a gaming environment and/or sporting environment.

The wearable system may be used to monitor one or more metabolic and/or cardiovascular parameters of a subject (as well as optionally one or more activity, exertion, and/or environmental parameters) in a gaming environment (e.g. during a video gaming session, during a paintball session, during a battlefield simulation, etc.) and/or in a sporting environment (e.g. during a training session, during a hockey game, during a marathon, etc.), during work in dangerous environments, etc.

Yet another illustrative example is the use of a wearable system in accordance with the present disclosure, for monitoring one or more metabolic and/or cardiopulmonary parameters of a subject just prior to, during and after taking a dose of a medication by the subject.

The wearable system may be used to monitor one or more metabolic and/or cardiovascular parameters of a subject (as well as optionally one or more activity, exertion, and/or environmental parameters) just prior to (e.g. in the minutes leading up to), during (e.g. while ingesting, inhaling, placement of a patch, etc.), and after (e.g. for minutes after, for hours after, etc.), taking a dose of the medication by the subject. Some non-limiting examples of medication include bronchodilators, beta blockade, intrinsic sympathomimetic drugs, steroids, vasodilators.

Yet another illustrative example is a wearable system in accordance with the present disclosure, configured to monitor one or more metabolic and/or cardiopulmonary parameters of a subject in a clinical trial. The wearable system may be configured to report subject data to a clinical trial coordinator, via user device, an external coordinating device, and/or a $3^{rd}$ pry service. Such data may be advantageous in determining the response of a subject to a therapy, changes in a disease state of a subject during a therapy, metabolic changes in the subject associated with a therapy (e.g. after taking a dosage of a medication), to capture early complications with a subject in a trial (e.g. a complication that could lead to withdrawal from the trial, or complications for the subject), or the like.

Yet another illustrative example is a wearable cardiac output monitor, including a plurality of sourcing electrodes configured to apply an electrical signal to the subject, and a plurality of sensing electrodes configured to pick-up bioelectrical signals from the body of the subject, the bioelectrical signals being at least partially related to the applied electrical signal. The CO monitor also includes a controller designed to generate and direct the electric signal to the body via the sourcing electrodes and to accept the bioelectric signals from the body via the sensing electrodes. The CO monitor may include means for extracting a signal relating to the cardiac output of the subject (e.g. heart rate, ventricular ejection time, stroke volume, a synchronization signal, a delay signal, etc.). In one non-limiting example the controller may be configured to generate and to deliver to the subject a bandwidth limited impulse signal (e.g. a band-limited impulse signal, chirp signal, etc. with significant signal amplitude between 10-200 kHz, between 20-150 kHz, between 50-90 kHz, etc.). The corresponding bioelectric signals are analyzed by the controller dependent upon the impulse to produce a corresponding band-limited impulse response signal, the phase and gain characteristics of which may be related to the cardiac output of the subject. Such testing may be synchronized with an activity signal (e.g. a gait signal, posture signal), and/or an exertion signal (e.g. a heart-beat, a respiratory beat, etc.), in order to provide an improved noise floor, to remove movement based signal corruption, etc.

The wearable cardiac output monitor may be configured to communicate wirelessly with a wearable system in accordance with the present disclosure. The cardiac output monitor and the wearable system may be placed onto the same subject. A user device, a communication system, etc. may be configured to aggregate simultaneously obtained metabolic and/or cardiopulmonary parameter data from an associated wearable system.

FIG. 1 shows a wearable system in accordance with the present disclosure for monitoring one or more metabolic and/or cardiopulmonary parameters of a subject 1. The wearable system includes a control unit 130 and a sampling module 110. The sampling module 110 connects to the control unit 130 and the subject 1. The sampling module 110 includes an interfacing component 120 for establishing contact with a breath stream of the subject 1. The sampling module 110 includes a lumen for communicating a breath gas sample from the subject 1 to the control unit 130. The control unit 130 is attached to an armband 140 for easy attachment to an arm of the subject 1. The control unit 130 includes communication means for communicating a wireless signal 150 with an external system (e.g. a user device, an external coordinating device, a communication system, etc.) and/or one or more additional sensors (e.g. a respiratory volume sensor, an ekg sensor, etc.). Alternatively the control unit 130 may be worn in a pocket 141, on a belt, as part of a neck cuff 145, etc. The control unit 130 may be integrated into an ear clip 143 and worn on the ear 3 of the subject 1.

FIGS. 2a-d show aspects of non-limiting examples of a sampling module in accordance with the present disclosure. FIG. 2a shows a cross-section of the head 5 of a subject indicating the nasal cavity 7 and oral cavity 13. A gas exchange region AA is indicated and highlighted in subsequent figures. A cross section of an interfacing component 220 (e.g. as included in a sampling module in accordance with the present disclosure), is shown positioned against the head 7 between the nasal cavity 7 and the oral cavity 13. In this example, a nasal breath gas stream 11 is shown passing through the nasal cavity 7 only. The interfacing component 220 is positioned so as to interface with this breath gas stream 11.

FIG. 2b shows an example of the gas exchange region AA in greater detail. The interfacing component 220 is positioned below the nasal cavity 7 in the nasal breath gas stream 11 of the subject. The interfacing component 220 includes a lumen 222 for exchanging a breath gas sample between the breath stream 11 of the subject and the control unit (as depicted in FIG. 1). The interfacing component 220 also includes a plurality of micro-holes 224 positioned along the wall of the lumen. The micro-holes 224 may be positioned so as to rest towards the head 5. Such orientation may be advantageous for minimizing the effect of environmental disturbances on the accuracy of the breath gas sample drawn from the breath stream 11 by the control unit 130. The interfacing component 220 may be partially constructed from a hydrophobic material so as to minimize ingress of biocontaminants and/or water in to the lumen 222 during use.

The micro-holes 224 may include hydrophobic filters suitable for preventing biocontaminants and/or water from entering the lumen 222 during use. In one example, the micro-holes 224 are at least partially formed from a microporous membrane material, with an average pore diameter of approximately 0.2 um.

The interfacing component 220 may be a micro-cannula in accordance with the present disclosure. A portion of the interfacing component 220 may also extend into the nasal cavity 7. The interfacing component 220 may include a sensor in accordance with the present disclosure (not explicitly shown), operably position able within the breath stream 11 so as to measure one or more dimensions (e.g. width, area, depth) of the nasal cavity 7.

FIG. 2c shows aspects of an alternative interfacing component 230 positioned against the head 5 just below the nasal cavity 7 of the subject 1. The interfacing component 230 may be well suited for use in an uncontrolled environment (e.g. outdoors). The interfacing component 230 includes a lumen 232 and shielded micro holes 234. The shielded micro holes 234 are suitable for sampling breath gases from the breath stream 11 without being subject to the direct influence of environmental winds, gusts, etc. that may be experienced by the wearable system in uncontrolled environments. The shape of the interfacing component 230 in this non-limiting example is altered so as to improve the repeatable placement along the head 5 during use. The micro holes 234 may include any of the aspects as described in FIG. 2b suitable for substantially preventing bodily fluids from entering the lumen 232.

FIG. 2d shows an alternative interfacing component 240 in accordance with the present disclosure, suitable for capturing breath gas samples from either the nasal cavity 11 or the oral cavity 13 of a subject. The interfacing component 240 is shown operably interfacing with the nasal breath stream 11 and the oral breath stream 15. The interfacing component 240 may include one or more lumens 242 for communicating the breath gas sample to the control unit 130. The shape of the interfacing component 240 may be drawn out so as to bridge the gap between the oral cavity 15 and the nasal cavity 7. The interfacing component 240 may include one or more micro-holes 244 arranged so as to be positioned towards the head 5 of the subject 1 and one or more shielded sample ports 246 positioned towards the oral cavity 13, the micro-holes 244 and the sample ports 246 collectively configured to interface with the breath streams 11, 15 of the subject 1.

The interfacing component 240 may include a plurality of lumens 240 with portions of the micro-holes 244 and sample ports 246 being in fluid communication with each lumen 240. In such an example, separate breath gas samples can be separately and simultaneously drawn from different breath streams of subject (e.g. from the oral cavity 13, the left/right aspects of the nasal cavity 7). In this example, each gas sample may be analyzed by a separate set of sensors to create a series of signals, each representative of a different breath stream of the subject. Such signals may be combined to assist the subject with breathing exercises, etc. during a workout, battlefield simulation, during labor, etc.

FIGS. 3a-d show aspects of a flow sensor 310 (or wireless flow sensor as described elsewhere in the present disclosure) in accordance with the present disclosure. The flow sensor 310 is configured for placement into the oral cavity 13 of the subject 1. The flow sensor 310 is generally configured to be minimally obstructive to the breathing of the subject 1 and may be configured so as to be fully place able within the oral cavity 13 of the subject 1.

FIG. 3a shows the flow sensor 310 operably positioned within the oral cavity 13 of the subject 1. The flow sensor 310 includes one or more channels through which the breath stream 15a, 15b of the subject will flow during use. The flow sensor 310 may be generally retained during use via a gentle bias and interlocking of the flow sensor 310 against the lips and teeth of the subject 1. The flow sensor 310 may further be designed so as to allow for the subject 1 to bite down on it during use, thus providing another means for hands free retention during a monitoring session.

FIG. 3*b* shows a cross section of the flow sensor 310 with some additionally highlighted details. The flow sensor 310 may include a manifold 320 for interfacing with the anatomy of the subject and for housing one or more sampling lines 347*a-b*. The manifold 320 may include lip retention features 333*a,b* and/or teeth retention features 335*a,b* so as to secure the flow sensor 310 within the oral cavity 13 of the subject 1 during use. One or more of the features 333*a,b*, 335*a,b* may be pre-molded to a desired shape (e.g. molded from a rubber material, thermoplastic elastomer, etc.). The features 333*a,b*, 335*a,b* may also be formed from a remoldable material (e.g. a wax, a thermoplastic elastomer, etc.) so as to be adjustably fitted to the subject 1 at the time of use.

The flow sensor 310 may include one or more diffusers 325*a,b* operably located substantially within the breath stream 15*a,b* configured so as to break-up turbulence in the flow stream, normalize the flow stream through the flow sensor 310 provide a partial obstruction with the flow stream, etc. The diffusers 325*a,b* are shown near the exit of the flow sensor 310 but may also be located within the perimeter of the flow sensor 310, across one or more channels, etc.

The flow sensor 310 may include one or more sampling ports 345*a,b* along the wall(s) of one or more channels suitable for interacting with the breath stream 15*a,b* as it operably passes through the flow sensor 310. The sampling ports 345*a,b* may be coupled with one or more associated sampling lines 347*a,b* and an electronics module 350. The sampling lines 347*a,b* may be configured to provide fluid communication between the breath stream 15*a,b* and the electronics module 350.

The electronics module 350 may include one or more sensors for interfacing with the sampling lines 347*a,b*. In aspects, the electronics module 350 may include one or more sensors in accordance with the present disclosure. Some non-limiting examples of such sensors include a gas sensor, a pressure transducer, microphone, temperature sensor, and the like. In one non-limiting example, the electronics module 350 includes a pressure transducer. One or more of the sampling lines 347*a,b* may be coupled to the pressure transducer so as to operably measure pressure differences within the breath stream 15*a,b* and/or between the interior of the oral cavity 13 and the surroundings. Thus a signal related to the flow velocity in the breath stream 15*a,b* of the subject 1 may be generated.

The electronics module 350 may further include means for monitoring the dimensions of one or more channels (e.g. via a reflective light source, etc.). A dimension of the channel may be used in combination with a flow velocity signal to produce a flow volume signal that may be further used in the assessment of one or more metabolic and/or cardiopulmonary parameters.

The electronics module 350 may include a wireless transceiver for wirelessly communicating one or more signals 355 with an external system (e.g. a control unit, a user device, an external coordinating device, a communication system, etc.).

In aspects, the flow sensor 310 may be integrated into an interfacing component 120 in accordance with this disclosure. In this example, the flow sensor 310 may include an electronics module 350, but equivalent functionality may be provided by a control unit 130 in accordance with the present disclosure. The sampling module 110 may include a means for communicating between the sampling ports 345*a,b* and the control unit 130. In aspects, a pressure transducer may be included in the control unit (e.g. as an adjunct sensor). In such aspects, the flow sensor 310 may be included into the interfacing component 120 and the sampling lines 347*a,b* may extend within the sampling module 110 so as to connect the pressure transducer, included in the control unit 130, with the sampling ports 345*a,b*.

The flow sensor 310 may include a grip element 360 for easy removal of the flow sensor 310 from the oral cavity 13 of the subject 1.

FIG. 3*c* shows a front view of a flow sensor 310 in accordance with the present disclosure. The flow sensor 310 includes a mesh diffuser 325*b* along with an electronics module 350 in accordance with the present disclosure, a manifold 320 and a grip element 360. The manifold 320 may be configured to substantially form a seal around the edges of the oral cavity 13 of the subject 1 so as to ensure the breath stream passes through the flow sensor 310 during use. FIG. 3*c* demonstrates an example of a wireless flow sensor, wherein the flow sensor 310 may communicate wirelessly with an external system (e.g. a control unit, a user device, an external coordination device, etc.).

FIG. 3*d* shows a non-limiting alternative of a flow sensor 310' optionally included within the interfacing component of a sampling module 110. The flow sensor 310' may interface with a micro-cannula 390 to provide fluid communication between an internally included channel and the control unit 130. The micro-cannula 390 may include a lumen through which a fluid sample 395 may flow during use. The flow sensor 310' is shown with a manifold 370, a diffuser 375*b*, an electronics module 380, and a grip element 385.

The electronics module 350, 380 may be reusable, in which case, it may be remove-ably place able within the flow sensor 310, 310'.

Figures 4, 5A, 5B, 6, 7:
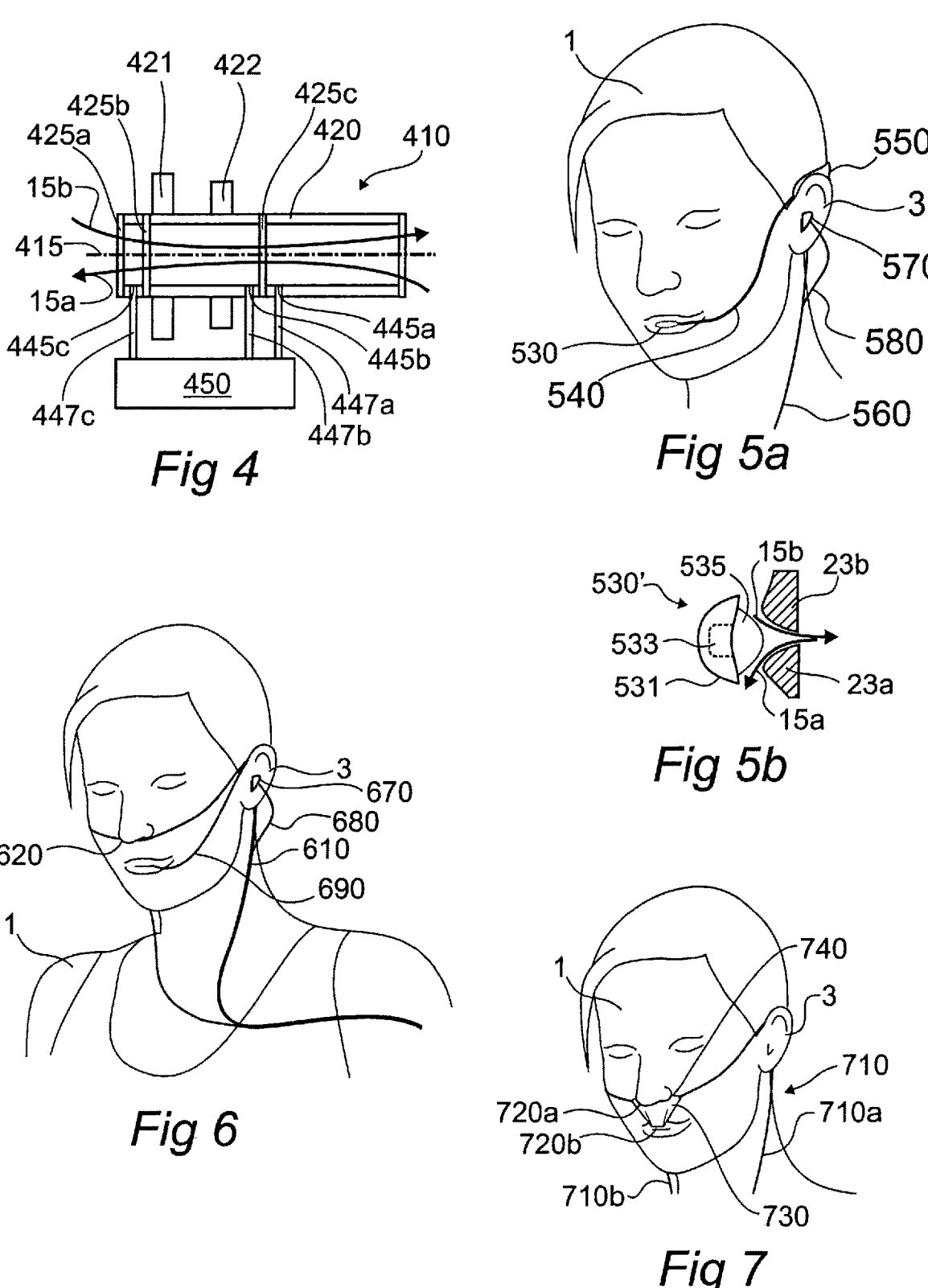
FIG. 4—Shows a schematic of a wireless flow sensor in accordance with the present disclosure.
FIGS. 5*a-b*—Show aspects of an example of a sampling module in accordance with the present disclosure.
FIG. 6—Shows an aspect of an example of a sampling module in accordance with the present disclosure.
FIG. 7—Shows an aspect of an example of a sampling module in accordance with the present disclosure.

FIG. 4 shows a schematic of a flow sensor 410 in accordance with the present disclosure. The flow sensor 410 may include a manifold 420 with a channel formed there through, through which the breath stream 15*a,b* of a subject 1 may pass during use. A guide line 415 is shown coaxial to the operable breath stream 15*a,b* so as to assist with the description. The flow sensor 410 may be substantially small enough to insert completely into the oral cavity of a subject. The flow sensor 410 may be connected to an electronics module 450 via the sampling lines 447*a-c*, the sampling lines 447*a,c* interfacing with the channel via one or more associated sampling ports 445*a-c*. In this non-limiting example, starting from the outside of the subject 1 and moving in the direction of the oral cavity along the guide line 415, the flow sensor 410 may include a diffuser 425*b* (e.g. to substantially protect the channel from the surrounding environment), the sampling port 445*c* (e.g. to sample breath gas from the breath stream 15*a,b* of the subject 1), a second diffuser 425*a* (e.g. to prevent contaminants from contacting the sampling port 445*c*), a lip retaining feature 421 (e.g. for placement between the lips and the teeth), a tooth retaining feature 422 (e.g. for placement behind the teeth), a sampling port 445*b*, a partial obstruction 425*c* (e.g. for operably creating a measurable pressure difference between the sampling ports 445*a,b*), and a sampling port 445*c*.

The electronics module 450 may be configured to monitor a breath gas sample via a gas sensitive sensor (e.g. a sensing membrane) coupled to the sampling line 447*c*, pressure differences via one or more pressure transducers (e.g. a differential MEMs pressure sensor) coupled to one or more sampling lines 447*a-c* (and optionally an ambient pressure). In aspects, the electronics module 450 may be included in a control unit 130 in accordance with the present disclosure and the sampling lines 447a-c may be included within an associated multi-lumen sampling module 110 to provide fluid communication between the sampling ports 445a-c and one or more sensors included within the control unit 130.

FIGS. 5a-b show aspects of examples of a sampling module in accordance with the present disclosure. FIGS. 5a-b show a sampling module configured as a boom element suitable for placement within the breath stream of a subject 1.

FIG. 5a shows a sampling module 540 as mounted on the face of a subject 1. The sampling module 540 includes an interfacing unit 530, optionally an ear bud 570, and one or more elongated portions 560, 570. The elongated portions 560, 570 may be suitable for communicating between the interfacing component 530, or the ear bud 570 and a control unit (not explicitly shown). The ear bud 570 may be provided in accordance with the present disclosure configured for placement into the ear 3 of the subject 1. The ear bud 570 may include a speaker element for communicating with the subject 1 during operation. The ear bud 570 may include an activity sensor and/or an exertion sensor in accordance with the present disclosure.

FIG. 5b shows a close-up of an interfacing component 530, 530' for sampling breath gases from the oral breath stream 15a,b of the subject 1. The interfacing component 530, 530' may include a lumen 533 for drawing a sample from the breath stream 15a,b, a shield 531 for protecting the sampling zone from surrounding wind gusts, etc., and a filter element 535 for protecting the lumen 533 from moisture, biocontaminants, etc. that may be present in the breath stream 15a,b.

The lumen 533 may include a gas sensing membrane in accordance with the present disclosure. The sampling module 110, 540 may include an emitter and detector for monitoring the gas sensing membrane and communicating an associated signal to the control unit 130 for further processing.

The filter element 535 may include a hydrophobic micro-porous membrane for limiting fluid ingress into the lumen 533. The micro-porous membrane may have a dramatically enhanced active area, which may be advantageous for extending the life of the filter element 535.

The sampling module 540 may include a mounting element 550 for securement to the ear 3 of the subject 1.

FIG. 6 shows aspects of a sampling module 610 in accordance with the present disclosure. The sampling module 610 includes an oral elongated portion 690 optionally including a lumen for communicating with an interfacing component (not explicitly shown) placed within the oral cavity of the subject 1. The sampling module 610 may include one or more lumens for providing fluid communication between the control unit 130 and a patient interface. The sampling module 610 may include a nasal interfacing component 620 for capturing breath gas samples from the nasal flow stream of the subject 1. The sampling module 610 may further include an ear bud 670 in accordance with the present disclosure, and a branched elongate element 680 for communicating with the ear bud 670. The nasal interfacing component 620 may include a left nostril interface and a right nostril interface for separable sampling of the breath stream associated with each nostril of the subject 1.

The sampling module 610 may be advantageous for the separate sampling of breath gases from the nasal and oral cavities of the subject, as well as communicating with the subject via the ear bud 670 and/or measuring one or more physiological parameter of the subject via one or more sensors included in the ear bud 670.

FIG. 7 shows aspects of a sampling module 710 for monitoring the breath stream of a subject 1. The sampling module 710 includes two micro-cannulas 710a, 710b, which may be worn over the ears 3 of the subject 1. The sampling module 710 also includes an interfacing component 740 for simultaneously sampling gases from the nasal breath stream and the oral breath stream of the subject 1. The interfacing component 740 may include sampling ports 720a for interfacing with the nasal breath stream and sampling ports 720b for interfacing with the oral breath stream.

The sampling module 710 may be advantageous for providing a secure and unobtrusive means for sampling breath gases from the subject 1.

FIGS. 8a-g show portions of sampling modules 820, 840, 860, 880, 890 in accordance with the present disclosure. The sampling module 820, 840, 860, 880, 890 includes a mouth-guard for placement within the oral cavity of the subject 1. The sampling module 820, 840, 860, 880, 890 may be advantageous for offering reasonably un-obtrusive gas sampling from the subject, while optionally providing the protective functionalities of a mouthguard.

Figures 8A, 8B, 8C, 8D, 8E, 8F, 8G:
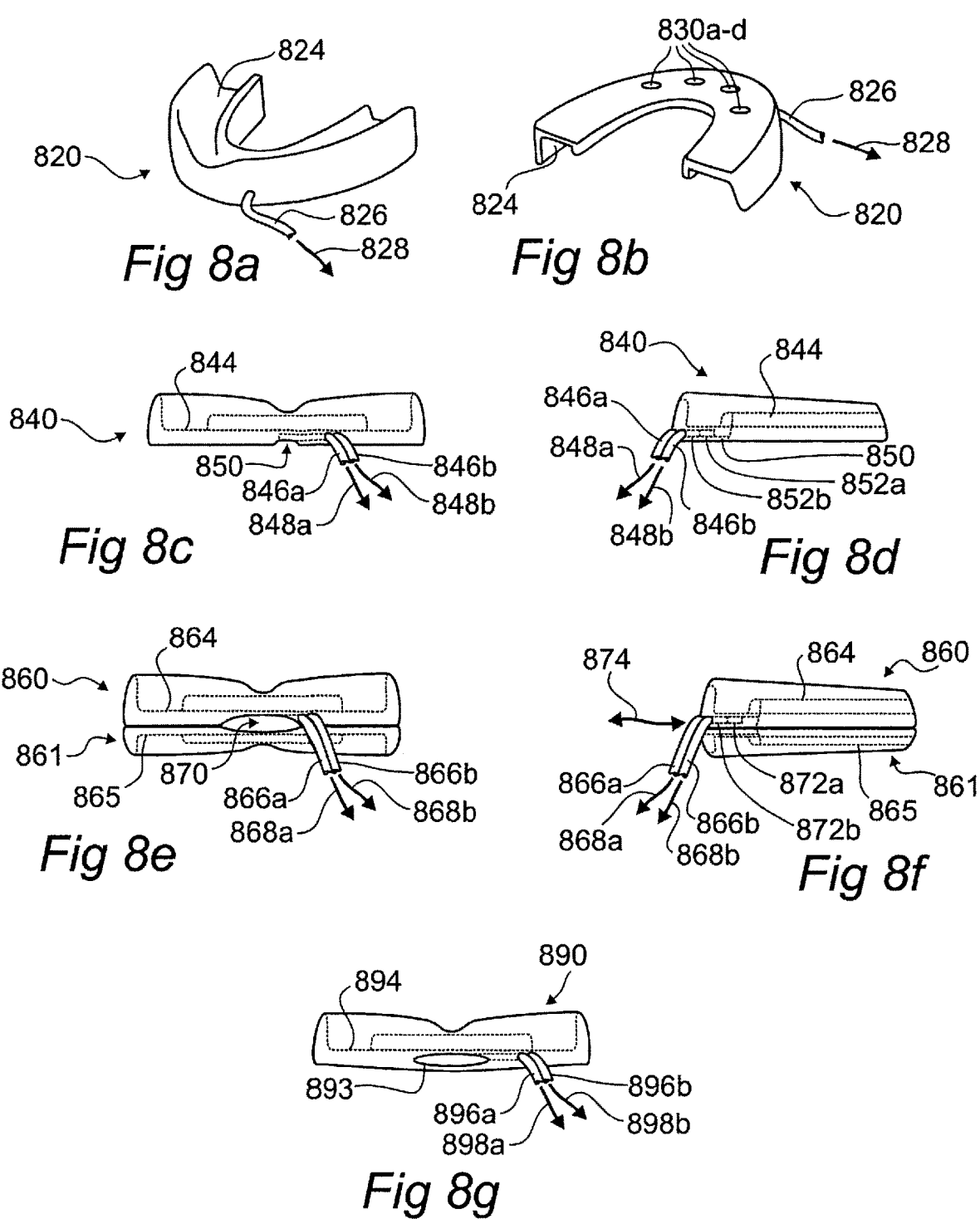
FIGS. 8*a-g*—Show aspects of examples of a sampling module in accordance with the present disclosure.

FIG. 8a shows a portion of a sampling module 820 with a micro-cannula 826 for operably communicating a fluid sample 828 between the subject and a control unit 130. The sampling module 820 also includes a trough 824 for interfacing with the teeth of the subject 1. In one non-limiting example, the trough 824 may be remoldable (e.g. formed from a remoldable thermoplastic elastomers, SEBS, styrenic block copolymers, polyolefin blends, elastomeric alloys (TPE-v or TPV), thermoplastic polyurethanes, thermoplastic copolyester and thermoplastic polyamides as provided under the trade names Arntitel (DSM), Engage (Dow chemical), Hytrel (Du Pont), or Kraton).

FIG. 8b shows an alternative view of the sampling module 820, more clearly highlighting a plurality of sampling ports 830a-d coupled to the micro-cannula 826. The sampling ports 830a-d may be arranged on the interfacing component of the sampling module 820 so as to rest near the exit of the oral cavity of the subject 1 during use. This configuration may be advantageous for limiting ingress of saliva into the sampling ports 830a-d during use. The sampling ports 830a-d may include one or more hydrophobic micro-porous plugs and/or membranes to substantially minimize ingress of biocontaminants and/or liquids into the lumen of the micro-cannula 826 during use.

FIG. 8c shows a portion of a sampling module 840 with a trough 844 for mounting to the teeth of a subject 1, a flow channel 850 for directing the oral breath stream over the sampling module 840, and two sampling lines 846a,b (or alternatively a multi-lumen micro-cannula), for communicating 848a,b between the sampling module and one or more sensors, a control unit, etc. The sampling lines 846a,b may be arranged so as to be positioned along the breath stream of the subject during use.

FIG. 8d shows an side view of the sampling module 840 including a trough 844, a flow channel 850, and two sample lines 846a,b that operably interact with the breath stream of the subject 1 via associated sample ports 852a,b. The sample ports 852a,b may include filter elements to substantially inhibit the ingress of contaminants into the sample lines 846a,b. The sample lines 846a,b may communicate 848a,b with one or more sensors, a control unit, etc. In one non-limiting example, the sample lines 846a,b may interact with one or more pressure transducers. The pressure transducers may be arranged to operably measure pressure gradients along a breath stream of a subject, measure differences in the pressure within points of a breath sample and the surroundings, etc. The resulting signals may be used to process one or more flow related metabolic and/or cardiopulmonary parameters from the subject.

FIGS. 8*e-f* show frontal and side views of a portion of a sampling module including an intra-oral interfacing component with an upper piece 860 and a lower piece 861. The upper piece 860 and the lower piece 861 may be configured to form a closed flow channel 870 with a controlled dimension when placed inside the oral cavity of a subject 1. The flow channel 870 may include one or more sampling ports 872a,b arranged substantially along its length, the sampling ports 872a,b connected to associated sampling lines 866a,b in communication 868a,b with one or more sensors, a control unit, etc. The upper piece 860 includes an upper trough 864 for interfacing with the upper teeth of the subject and the lower piece 861 includes a lower trough 865 for interfacing with the lower teeth of the subject 1. The flow channel 870 of known dimension may be advantageous for assisting in converting a breath flow velocity into a breath volume rate measurement for use in calculating a metabolic and/or cardiopulmonary parameter of the subject 1.

FIG. 8*g* shows a portion of a sampling module 890 in accordance with the present disclosure formed into an intra-oral interfacing component, including a trough 894, two sampling lines 896a,b, for communicating 898a,b with a sensor, a control unit, etc., and a central flow channel 893, configured so as to provide a conduit for the breath stream when secured into the oral cavity of a subject 1. The central flow channel 893 is interfaced with the sampling lines 896a,b so as to provide a means for monitoring the breath stream of the subject 1. The sampling module 890 may be advantageous for providing an intra-oral means for monitoring the breath stream of the subject 1, with a conduit of know dimension through which the breath sample flows during use and a substantially minimal profile.

The sampling lines 826, 846a,b, 866a,b, 896a,b may be integrated into a chin strap, a helmet strap, a pullout strap, etc. attached to the intra-oral portion of the sampling module. Such a configuration may be advantageous in that helps to minimize differences between currently employed sportswear and the changes introduced by a wearable system in accordance with the present disclosure.

Figures 9A, 9B, 10, 11A, 11B:
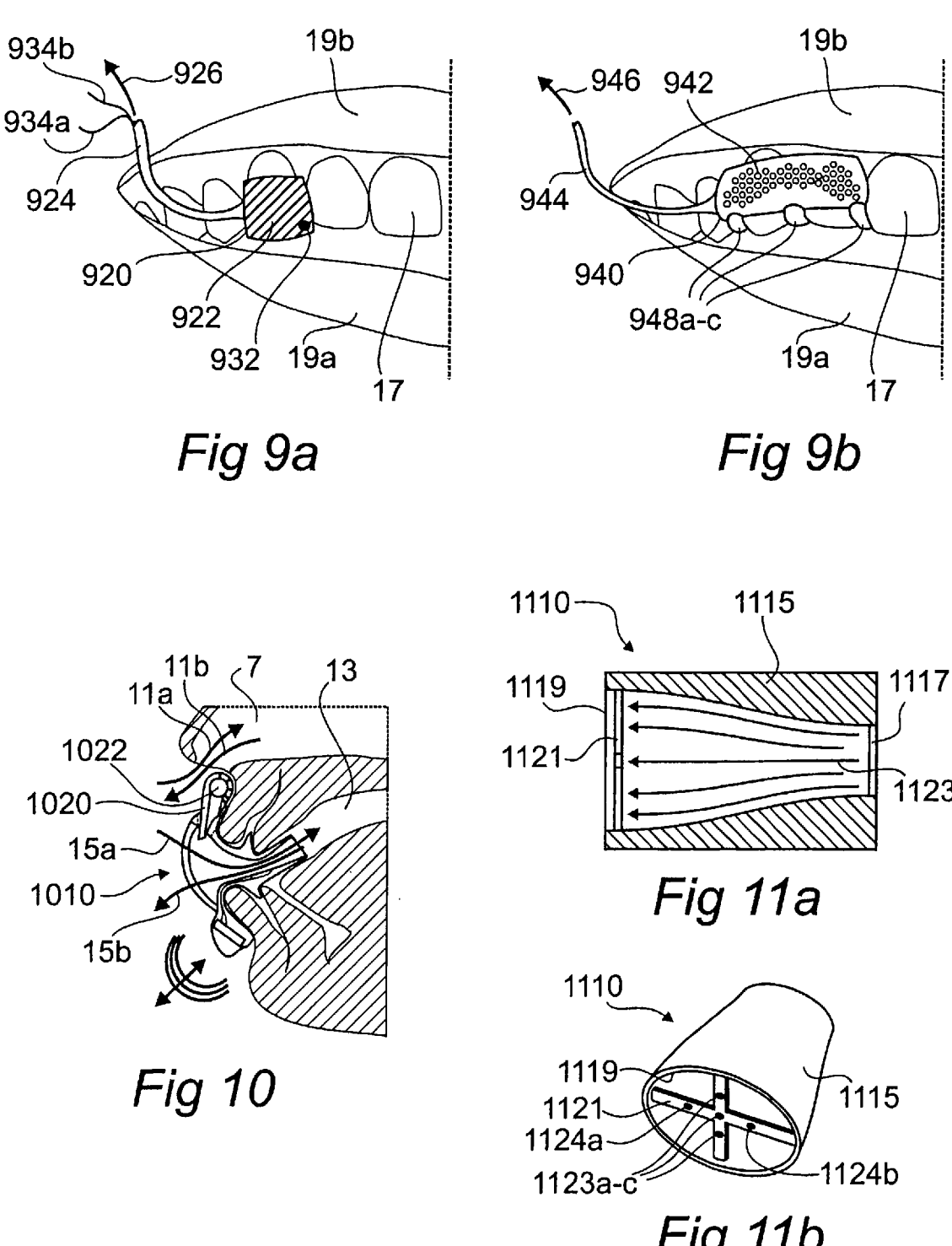
FIGS. 9*a-b*—Show aspects of examples of a sampling module in accordance with the present disclosure.
FIG. 10—Shows an aspect of a wearable system coupled with a wireless flow sensor in accordance with the present disclosure.
FIGS. 11*a-b*—Show schematics of an aspect of a sampling module and/or a wireless flow sensor in accordance with the present disclosure.

FIGS. 9*a-b* show portions of sampling modules in accordance with the present disclosure, suitable for intra-oral sampling of the breath stream of the subject. FIG. 9*a* shows an interfacing component 920 configured so as to be fastened to a tooth 17 of a subject. The interfacing component 920 included in a sampling module includes a filtered cover 922 configured to allow a breath gas sample to be drawn into the interfacing component 920. The filtered cover 922 may be formed from a hydrophobic filter material such as a micro-porous Teflon layer, a multilayered structure, a nonwoven polystyrene filter, etc. The interfacing component 920 may be formed as a pocket so as to slip over one or more teeth 17. Alternatively, additionally, or in combination, the interfacing component 920 may include a re-moldable material for accurate and comfortable fitting to one or more teeth of the subject.

The interfacing component 920 may include one or more sensory elements 932 adapted to measure one or more physiological or dimensional parameters of the subject during use. Some non-limiting physiological parameters include temperature, a flow parameter (e.g flow velocity, flow acoustic, a pressure level, a breath gas constituent, etc.), a pallet parameter (e.g. a pallet color, pallet tone), a body acoustic parameter (e.g. an audible breathing parameter, an audible heart-rate, etc.), a motion parameter, a bite parameter (e.g. a bite strength), and the like. Some non-limiting dimensional parameters include a lineal gap (e.g. distance from tooth to pallet, distance from cheek to cheek, etc.), an oral cavity volume, and the like. Some non-limiting examples of sensory elements 932 to monitor one or more of the parameters include a thermocouple, an thermopile, a humidity sensor, a microphone, a moisture sensor, a thermal mass flow sensor, an accelerometer, a fluorescent sensing film, photo-optical sensors, and the like.

In one non-limiting example, the sensory element 932 is a moisture sensor, the sensory element 932 may be located just within the filtered cover 922 and may be advantageous for generating a control signal suitable for controlling fluid flow into the interfacing component 920, reversing sampling flow so as to reverse a blockage, etc.

In another non-limiting example, the sensory element 932 is a temperature sensor for measuring the temperature of the breath stream of the subject during use. The subject may close his/her lips 19a,b and hold his/her breath for a period of time, after which the subject may exhale in a steady fashion. The temperature sensor may monitor the temperature of the flow stream during this procedure and produce a signal, at least partially related to the core body temperature of the subject during the monitoring session. In another non-limiting example, the subject may close his/her lips and breath nasally for a period of time. During that period of time, the sensory element 932 may monitor pressure changes in the oral cavity of the subject and produce a signal, at least partially related to the core body temperature of the subject during the monitoring session.

In the non-limiting example shown in FIG. 9*a*, the interfacing component 920 is connected to a micro-cannula 924 for communicating between the breath stream of the subject and the control unit. The micro-cannula 924 includes a lumen for communicating a breath gas sample 926 between the interfacing component 920 and the control unit. The micro-cannula 924 includes a plurality of micro-wires 934a,b for communicating one or more signals between the sensory element 932 and the control unit. The micro-wires 934a,b may be embedded into the walls of the micro-cannula 924, collocated with the lumen, run within one or more additional lumens, etc.

Although the filtered cover 922 is shown here on the outward facing side of the teeth 17, the filtered cover 922 may be placed on the inward facing side of the teeth 17, near the gum line, integrated into a molar bite bar, so as to rest near the roof of the mouth, under the tongue, etc.

FIG. 9*b* shows an interfacing component 940 configured so as to be intra-orally clamped onto one or more teeth 17 of the subject. The interfacing component 940 includes a filtered cover 942 configured so as to interface with the breath stream of the subject. The filtered cover 942 is shown with an array of micropores, configured so as to allow gas exchange between the interfacing component 940 and the breath stream of the subject. The interfacing component 940 may be formed so as to tightly contour to the teeth 17 of the subject, such that the subject can comfortably close his/her lips 19a,b during use.

Although shown positioned against the outward facing side of the teeth 17, the filtered cover 942 may be configured for placement on the inward facing side of the teeth 17, near the gum line, integrated into a molar bite bar, etc. so as to rest near the roof of the mouth, under the tongue, etc.

The interfacing component 940 includes a plurality of clip elements 948a-c, configured so as to contour to the teeth 17 and to retain the interfacing component 940 in place during use. The clip elements 948a-c may include one or more retaining wires (e.g. a stainless steel wire, a shape memory wire, a nickel-titanium wire, etc.), optionally coated with one or more layers of a polymer, an elastomer, or the like. The clip elements 948*a-c* may be formable during placement so as to conform tightly yet comfortably to the teeth 17. The clip elements 948*a-c* may include one or more padded elements configured so as to substantially minimize discomfort for the subject during use.

In the non-limiting example shown in FIG. 9*b*, the interfacing component 940 is connected to a micro-cannula 944 for communicating between the breath stream of the subject and a control unit. The micro-cannula 944 includes a lumen for communicating a breath gas sample 946 between the interfacing component 940 and the control unit.

The interfacing component 940 may include a sensory element and associated micro-wires (not explicitly shown) in accordance with the sensory element 932 and associated micro-wires 934*a,b* as described in FIG. 9*a*.

FIG. 10 shows aspects of an interfacing component 1020 of a wearable system coupled to a wireless flow sensor 1010 in accordance with the present disclosure. The wireless flow sensor 1010 is coupled to the oral cavity 13 of the subject so as to monitor the breath stream 15*a,b* of the subject during use. The wireless flow sensor 1010 may include one or more sensors, electronics, and/or a wireless communication module to communicate one or more signals with a control unit, a user device, a communication system, or the like.

The interfacing component 1020 may include a lumen 1022 for communicating a breath gas sample through an associated sampling module, to a control unit, etc. The interfacing component 1020 may include a plurality of sample ports for interfacing with the nasal breath stream 11*a,b* and the wireless flow sensor 1010. The wireless flow sensor 1010 may include an access port by which the interfacing component 1020 can access the oral breath stream 15*a,b* and capture breath gas samples therefrom during use.

FIGS. 11*a-b* show schematics of an aspect of an interfacing component 1110 and/or a wireless flow sensor in accordance with the present disclosure for operable placement into a nasal or oral cavity of a subject during use.

FIG. 11*a* shows a cross sectional schematic of the interfacing component 1110 for placement into an oral or nasal cavity of a subject. The interfacing component 1110 includes a manifold 1115 configured to seal against the wall of the nasal or oral cavity of the subject. The manifold 1115 may be constructed from a re-moldable material, such as a thermoplastic elastomer, a wax, etc. The manifold 1115 includes a channel 1119 configured so as to direct the flow stream 1123 of the subject during use. The channel 1119 may include a changing profile so as to slow or accelerate the flow stream 1123 during use. The channel 1119 includes a support structure 1121 onto which one or more sensors and/or sample ports may be arranged. The channel 1117 may also include one or more diffusers 1117 to break-up and/or otherwise control the flow stream 1123 during use. The diffuser 1117 may include a mesh, a filter, etc. to substantially keep contaminants and/or fluids away from the interior of the channel 1119 during use.

FIG. 11*b* shows an alternative view of the interfacing element 1110 to highlight aspects of the support structure 1121. The support structure 1121 may be configured so as to cross the channel 1119 while providing a partial obstruction. The support structure 1121 includes one or more sensors 1123*a-c* and/or sample ports 1124*a,b* and means for communicating between the sensors 1123*a-c*, the sample ports 1124*a,b* and an electronics module, a sensory module, a control unit, a user device and/or a communication system in accordance with the present disclosure. The sensors 1123*a-c* may be adapted to measure one or more physiological or dimensional parameters of the subject during use. Some non-limiting physiological parameters which may be measured include temperature, a flow parameter (e.g flow velocity, flow acoustic, a pressure level, a breath gas constituent, etc.), a pallet parameter (e.g. a pallet color, pallet tone), a body acoustic parameter (e.g. an audible breathing parameter, an audible heart-rate, etc.), a motion parameter, a bite parameter (e.g. a bite strength), and the like. Some non-limiting dimensional parameters include a lineal gap (e.g. distance from tooth to pallet, distance from cheek to cheek, etc.), an oral cavity volume, and the like. Some non-limiting examples of sensors 1123*a-c* to monitor one or more of the parameters include a thermocouple, an thermopile, a humidity sensor, a microphone, a moisture sensor, a thermal mass flow sensor, an accelerometer, a fluorescent sensing film, and the like.

In one non-limiting example, at least one sensor 1123*a-c* may be a pressure sensor for measuring the pressure differential along the flow of the breath stream or between a site along the breath stream and an ambient reading during use.

The sample ports 1124*a,b* may be configured so as to accommodate extraction of a breath gas sample from the breath stream during use. Alternatively, additionally or in combination, the sample ports 1124*a,b* may be connected in fluid communication with one or more pressure transducers, to capture a differential pressure reading related to at least a flow characteristic of the breath stream.

Figures 12, 13A, 13B:
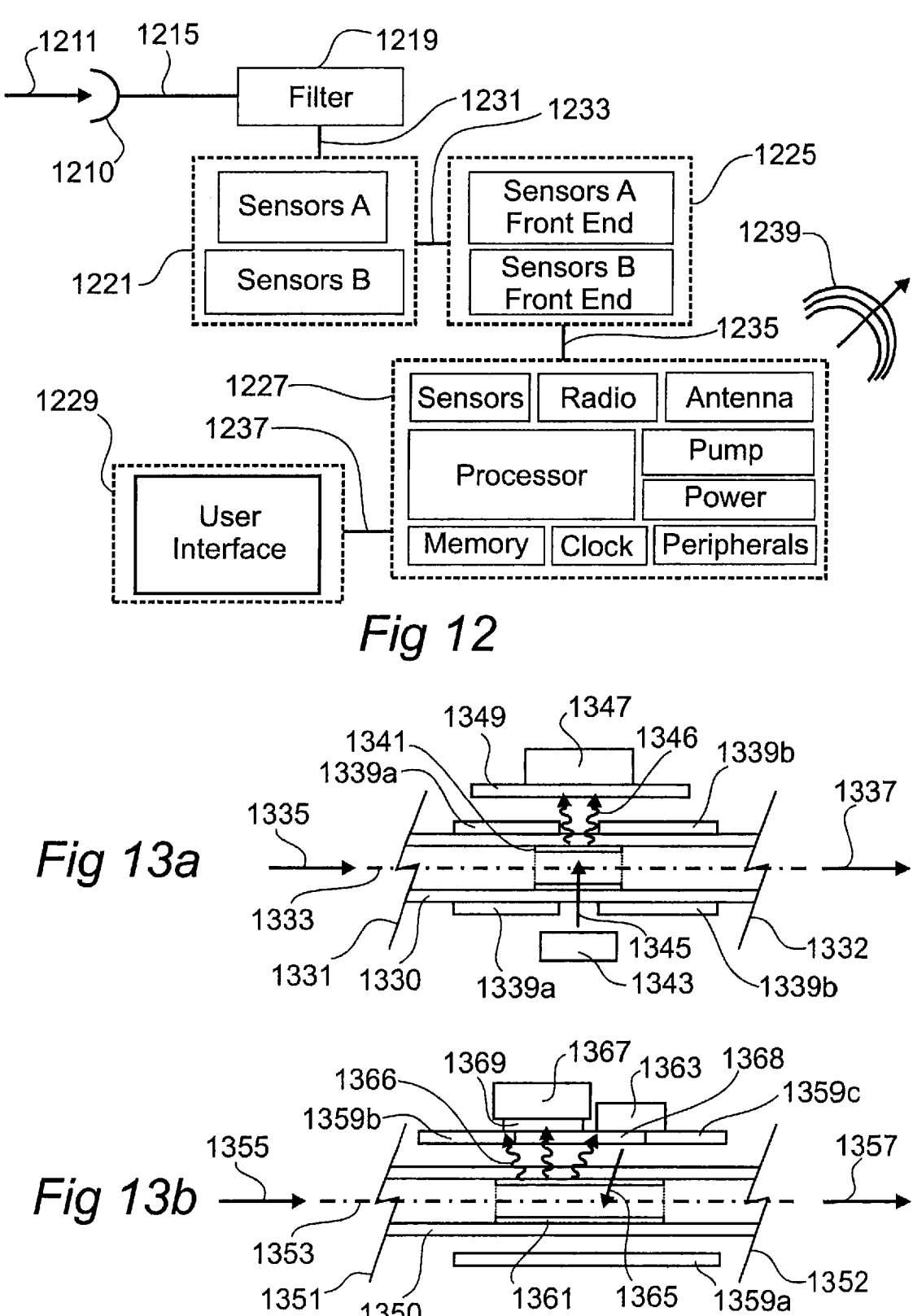
FIG. 12—Shows a schematic of a wearable system in accordance with the present disclosure.
FIGS. 13*a-b*—Show schematics of aspects of a sampling module in accordance with the present disclosure.

FIG. 12 shows a schematic of a wearable system in accordance with the present disclosure. The wearable system includes an interfacing component 1210 for capturing information from a breath stream 1211 of a subject. The interfacing component 1210 may include one or more sensory elements. The interfacing component 1210 communicates (e.g. via fluid communication, electrical communication, etc.) information related to the breath stream (e.g. a breath gas sample, a sensory output signal, etc.) along a first conduit 1215 (e.g. a micro-cannula, a micro-cable, etc.) to an optional filter element 1219. The filter element 1219 is configured to substantially remove one or more biocontaminants and/or water from the sample before passing it to an optional second conduit 1231 (e.g. a multi-lumen conduit, a micro-cannula, a micro-cable, etc.). The conduit 1231 may be configured so as to connect the sample with a sensor bank 1221. The sensor bank 1221 may include one more sensing membranes (e.g. Sensors A) in accordance with the present disclosure arranged so as to physically contact the sample during use. The sensor bank 1221 may also include one or more adjunct sensors (e.g. Sensors B) in accordance with the present disclosure. The sensing membranes and/or adjunct sensors may be arranged so as to be substantially in contact with associated electronics (e.g. emitters, detectors, signal conditioning electronics, etc.). Alternatively, additionally, or in combination, the sensor bank 1221 may be connected 1233 (e.g. via an optical window, a transparent wall, an electrical wire, etc.) to a conditioning bank 1225. The conditioning bank 1225 may include electronics, emitters and detectors (e.g. Sensors A Front End) for generating signals from the response of the sensing membranes (e.g. Sensors A) to the sample. The conditioning bank 1225 may include electronics, sources, sinks, ADCs, etc. (e.g. Sensors B Front End) for generating signals from one or more of the adjunct sensors (e.g. Sensors B).

The conditioning bank 1225 may communicate, via an interconnect 1235 (e.g. via electrical interconnects, an optical circuit, an RF circuit, etc.), one or more associated signals with a control module 1227 for further processing. The control module 1227 may also be arranged in fluid communication 1234 (e.g. via a fluid connector, a conduit, etc.) with the sensor bank 1221.

In aspects, the control module 1227 may include sensors (e.g. adjunct sensors, exertion sensors, sensing membranes, gas analyte sensors, etc.) in accordance with the present disclosure. The control module 1227 may also include a processor, a pump, a memory element, a power supply, a clock source, various peripherals (e.g. conditioning circuitry, communication circuitry, power management circuitry, etc.), a radio, an antenna, combinations thereof, and the like. The control module 1227 may also communicate 1237 (e.g. via an electrical interconnect) with a user interfacing module 1229 including one or more user interfacing elements (e.g. leds, ear bud speakers, microphones, etc.).

The control module 1227 may include a pump (e.g. a micropump, a piezoelectric micropump, etc.) in accordance with the present disclosure, for drawing a breath gas sample from the breath stream 1211, through the sensor bank 1221 and into the control module 1227. The control module 1227 may also include one or more sensors (e.g. adjunct sensors, sensing membranes, gas analyte sensors, etc.) in fluid communication with the operable flow path of the sample. Such sensor configurations may be advantageous to further enhance, calibrate or contribute to the measurement of one or more of the metabolic and/or cardiopulmonary signals of the subject during use.

The control module 1227 may include a radio and antenna both in accordance with the present disclosure for communicating one or more wireless signals 1239 with an external entity (e.g. a user device, a communication system, an external coordinating device, etc.).

The wearable system may be divided into one or more different configurations so as to form a practical system for implementation in a range of applications. In aspects, the wearable system may include a sampling module and a control unit both in accordance with the present disclosure. The sampling module may include one or more interfacing components 1210, the conduits 1215, 1231, the filter 1219, the sensor bank 1221, at least a portion of the communication means 1233, and the fluid interconnect 1234. The control unit may include the conditioning bank 1225, the control module 1227 and optionally the user interfacing module 1229 and associated communication means 1237 (e.g. wires, fiber optics, infrared transmitters, etc.).

In aspects, the sampling module may include the user interfacing module 1229 and associated communication means 1237 (e.g. with a connector for interconnecting with the control module 1227).

The examples described may be advantageous for forming a cost effective wearable system with a reusable part (e.g. the control unit) and a single use or limited use part (e.g. the sampling module).

FIGS. 13*a-b* show schematic aspects of a sampling module in accordance with the present disclosure. The sampling module shown in FIG. 13*b* includes a tube 1330 (e.g. a micro-cannula, a multi-lumen cannula, a micro-tube, etc.) with a lumen having an axis 1353. The tube 1330 may be configured so as to provide a path for an inbound sample 1335 from the subject side of the sampling module towards a sensing membrane 1341 in accordance with the present disclosure. The tube 1330 may also provide a path for an outbound sample 1357 to continue onto the control unit (not explicitly shown). The sensing membrane 1341 may be attached to the walls of the lumen (e.g. coated onto, glued to, etc.). The sampling module may also include one or more shrouds 1339*a,b* configured so as to substantially reduce ambient light from reaching the sensing membrane 1341 during use. The shrouds 1339*a,b* may be substantially optically opaque over the wavelengths of interest for exciting and/or sampling from the sensing membrane 1341. The sampling module may include a plurality of sensing membranes 1341.

The sampling module and/or control unit may include an emitter 1343 in accordance with the present disclosure, directed so as to operably deliver an excitation signal 1345 (e.g. visible light, ultraviolet light, near infrared light, etc.) to the sensing membrane 1341. The sensing membrane 1341 responds by emitting a fluorescent signal 1346, at least a portion of which is operably collected by a detector 1347 in accordance with the present disclosure, included in the sampling module or the control unit. The sampling module or the control unit may also include an optical filter 1349 for selectively preventing ambient light and/or emitter light wavelengths from reaching the detector 1347 during use.

In aspects, the sampling module may include an identification component (not explicitly shown) in accordance with the present disclosure, integrated into the tube 1330 or a connector between the sampling module and a control unit.

In one non-limiting example, the emitter 1343, detector 1347 and optical filter 1349 may be included in a control unit in accordance with the present disclosure. The tube 1330, sensing membrane 1341 and shrouds 1339*a,b* may be included in a sampling module in accordance with the present disclosure. Such a configuration may be advantageous for providing technically advanced, yet cost effective monitoring of breath gas samples. The sampling module may include an identification component such that the control unit may automatically calibrate the signals when operably connected with a new disposable sampling module.

In another non-limiting example, the emitter 1343, detector 1347, optical filter 1349, and optional control/conditioning circuitry (not explicitly shown) may be included in a sampling module in accordance with the present disclosure. The sampling module may further include a connector for operably interfacing the emitter 1343 and detector 1347 with an associated wearable control unit.

FIG. 13*b* shows a non-limiting alternative aspect of a sampling module and optionally a control unit. The sampling module includes a tube 1350 with a lumen, the lumen having a central axis 1353. The tube 1350 may be configured to provide a path for an incoming sample 1355 from the subject and a path for an outgoing sample 1357 to continue on to the control unit (e.g. via a connector, etc.). The sampling module may include a sensing membrane 1361 arranged along the wall of the lumen so as to operably interface with a passing breath gas sample. The sensing membrane 1361 may alternatively be supported on a member, a 3D lattice, integrated into a non-woven filter element, bound to a fin or flow disrupting element, or the like within the lumen of the tube 1350.

The sampling module or the control unit may include an emitter 1363 configured to operably direct an excitation signal 1365 towards the sensing membrane 1361, which may be include one or more responsive materials configured to generate a fluorescent signal 1366 and/or a change a chromatic property (e.g. a spectral absorbance, etc.) in response. The fluorescent signal 1266 may depend on one or more property of the incoming sample 1355 along with the excitation signal 1365. The detector 1367 may be configured to operably monitor the fluorescent signal 1266 and generate a signal related the one or more properties of the incoming sample 1355 suitable for further processing. The detector 1367 may include an optical filter 1369 configured to substantially remove one or more ambient and/or emitter signals 1345.

The control unit or the sampling module may include one or more mounting plates 1359a,b,c, and optionally one or more windows 1368. The mounting fixtures 1359a,b,c may be configured so as to at least partially enclose the tube 1350 when operably interconnected. The window 1368 may include an additional optical filter, an ambient light filter, etc. The mounting fixtures 1359a,b,c may be configured so as to snuggly and/or repeatably hold the tube 1351 in place during operable interconnection between the mounting fixtures 1359a,b,c and the tube 1351.

In one non-limiting example, the emitter 1363, the detector 1367, and the mounting fixtures 1359a,b,c may be included in the control unit and arranged so as to snuggly fit with a mating sampling module. This configuration may be advantageous for coupling a disposable sampling module with a reusable control unit.

FIGS. 14a-b show aspects of a sampling module in accordance with the present disclosure. FIG. 14a shows aspects of a sampling module including an interfacing component 1410, a conduit 1415, a filter 1417, a sensing membrane 1419 and a connector 1421 each in accordance with the present disclosure. The sampling module is configured to operably convey an incoming breath sample 1411 from the breath stream of a subject through to an outgoing breath sample 1423 heading into an associated control unit.

The control unit (not explicitly shown) may include a sensory electronics unit 1425 configured so as to operably monitor the sensing membrane 1419 when the control unit and the sampling module are inter-operably connected.

FIG. 14b shows aspects of a sampling module including an interfacing component 1430, a conduit 1435, a filter 1437, a sensing membrane 1439, a sensory electronics unit 1445, and a connector 1441 each in accordance with the present disclosure. The sampling module may be configured to operably convey an incoming breath sample 1411 from the breath stream of a subject through to an outgoing breath sample 1423 heading into an associated control unit. The connector 1443 may include a conduit for providing passage of the outgoing breath sample 1423 between the sampling module. The connector 1443 may include electrical interconnects 1447 to communicate between the control unit and the sensory electronics unit 1445.

The sensory electronics unit 1425, 1445 may include one or more emitters, one or more detectors, analog, digital and/or mixed signal conditioning circuits, power management circuits, compensation circuitry, and/or communication circuitry (e.g. I2C, SPI, units, etc.) each in accordance with the present disclosure in order to operably generate one or more relevant signals from the response of a sensing membrane 1419, 1439 for delivery to one or more elements of the control unit.

In one non-limiting example, the sensory electronics unit 1425, 1445 may include an emitter, for emitting light towards an associated sensing membrane 1419, 1439 about wavelength of 470 nm, and a detector for detecting a fluorescence signal and/or chromatic change in the sensing membrane 1419, 1439 during use. The sensory electronics unit 1425, 1445 may include a driver for substantially minimizing power consumption of the emitter during use, a signal conditioning front end which may include a transimpedance amplifier (optionally bootstrapped, with DC restoration, etc.), an integrating amplifier (e.g. a switched integrating amplifier), charge-sensing ADC, combinations thereof, or the like.

FIGS. 15a-c show examples of a wearable system in accordance with the present disclosure. FIG. 15a shows a subject 1501 wearing a piece of sporting equipment (e.g. a helmet 1503) with suitable mounting places for one or more aspects of a wearable system 1521, 1523, 1525, 1527. In aspects, the wearable system 1521, 1523, 1525, 1527 may be configured for attachment to a helmet 1503, a visor 1505, a chin guard 1509, a bar 1507, etc. In one non-limiting example, at least a portion of the wearable system 1521 may be integrated into the wall of the helmet 1503 so as to provide secure retention one the subject 1501 during use. The wearable system 1521 may include an intra-oral interfacing component in accordance with the present disclosure.

The wearable system 1521, 1523, 1525, 1527 may be embedded into the sporting equipment 1503, 1505, 1507, 1509 or attachable thereto (e.g. adhesively attachable, stitched, clipped to, etc.).

FIGS. 15b-c show a front view (FIG. 15b) and a side view (FIG. 15c) of a wearable system 1521, 1523, 1525, 1527 configured to monitor one or more metabolic and/or cardio-pulmonary parameters of the subject 1501. The wearable system 1521, 1523, 1525, 1527 may include a plurality of sensing membranes 1510a-d in accordance with the present disclosure, optionally covered by a filter 1520 (e.g. a biofluid filter, an optical filter, a combination thereof, etc.). The wearable system 1521, 1523, 1525, 1527 may further include a control unit 1526, a substrate 1515 and one or more electrical interconnects 1530 configured so as to electrically connect the sensing membranes 1510a-d to the control unit 1526.

The wearable system 1521, 1523, 1525, 1527 may be configured for placement within the breath stream 1511 (e.g. oral breath stream, nasal breath stream, etc.) of the subject 1501.

The control unit 1526 may include a power source, an emitter, a detector, etc. The substrate 1526 may include a waveguide for optically communicating between the emitter and the detector included within the control unit 1526 and one or more sensing membranes 1510a-d.

In another non-limiting example, the substrate 1526 may include one or more emitters and detectors positioned so as to emit and detect light towards or received from one or more associated sensing membranes 1510a-d. The electrical interconnects 1530 may electrically link the emitters, detectors and the control unit 1526.

The control unit 1526 may include one or more adjunct sensors (e.g. a humidity sensor, a barometer, a temperature sensor, etc.), and/or activity sensors (e.g. an accelerometer, etc.), a communication element (e.g. a microphone, a speaker, etc.).

The wearable system 1521, 1523, 1525, 1527 may include a radio and an antenna (e.g. included within the control unit 1526, and/or the substrate 1515) for communicating with an external entity (e.g. a user device, a communication system, an external coordinating device, etc.).

The filter 1520 may include a combination of a biocontaminant filter material for removing one or more biocontaminants and/or moisture from the breath stream 1511 and an optical filter material (e.g. a dye, a filler, etc.).

FIGS. 16-19 show schematics of aspects of a control unit, a user device, and an external coordination system in accordance with the present disclosure.

Figure 16:
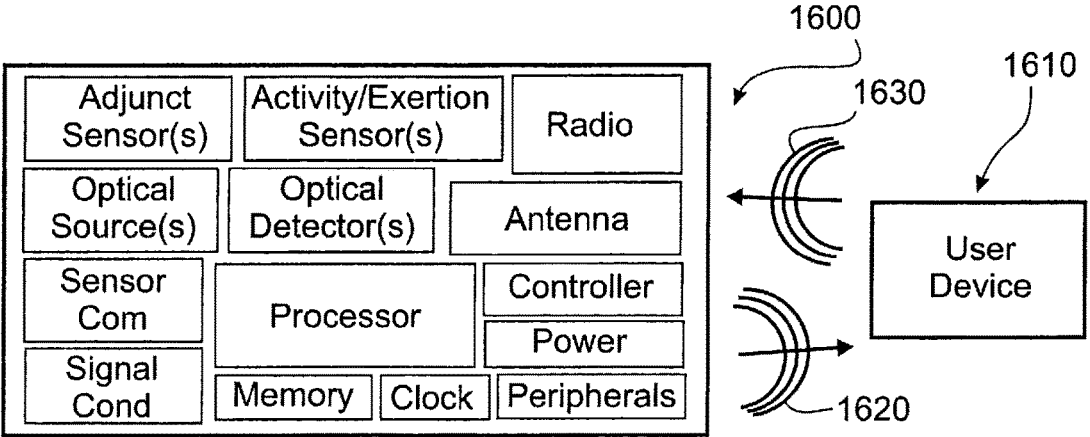
FIGS. 16-19—Show schematics of examples of a control unit, a user device and/or external coordination device, in accordance with the present disclosure.

FIG. 16 shows a schematic of aspects of a control unit 1600 in accordance with the present disclosure, including one or more adjunct sensors, activity and/or exertion sensors, optical sources (e.g. an emitter), optical detectors (e.g. a detector), a sensor communication unit, a signal conditioning unit, a processor, a memory element, a clock, one or more peripherals, a power source, power management circuitry, a controller, a radio and/or an antenna. The control unit 1600 is configured to communicate signals 1620, 1630 wirelessly with a user device 1610, an external coordination unit, etc.

Figure 17:
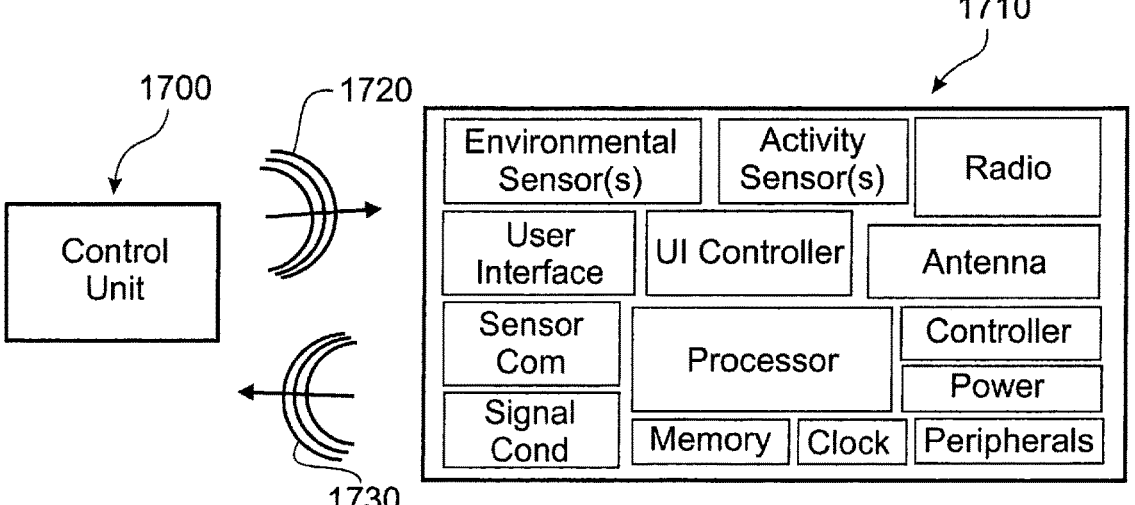

FIG. 17 shows a schematic of aspects of a user device 1710 in accordance with the present disclosure, including one or more environmental sensors (e.g a temperature sensor, humidity sensor, altimeter, etc.), one or more activity sensors (e.g. accelerometer, gyroscope, pedometer, etc.), a user interface (e.g. a speaker, a display, one or more LEDs, etc.), a user interface controller (e.g. a gesture capture element, an infrared sensor, a touch screen, etc.), a sensor communication unit, a signal conditioning unit, a processor, a memory element, a controller, a power supply, a clock source, one or more peripheral elements, a radio and an antenna. The user device 1710 is configured to communicate signals 1720, 1730 wirelessly with a control unit 1700.

Figure 18:
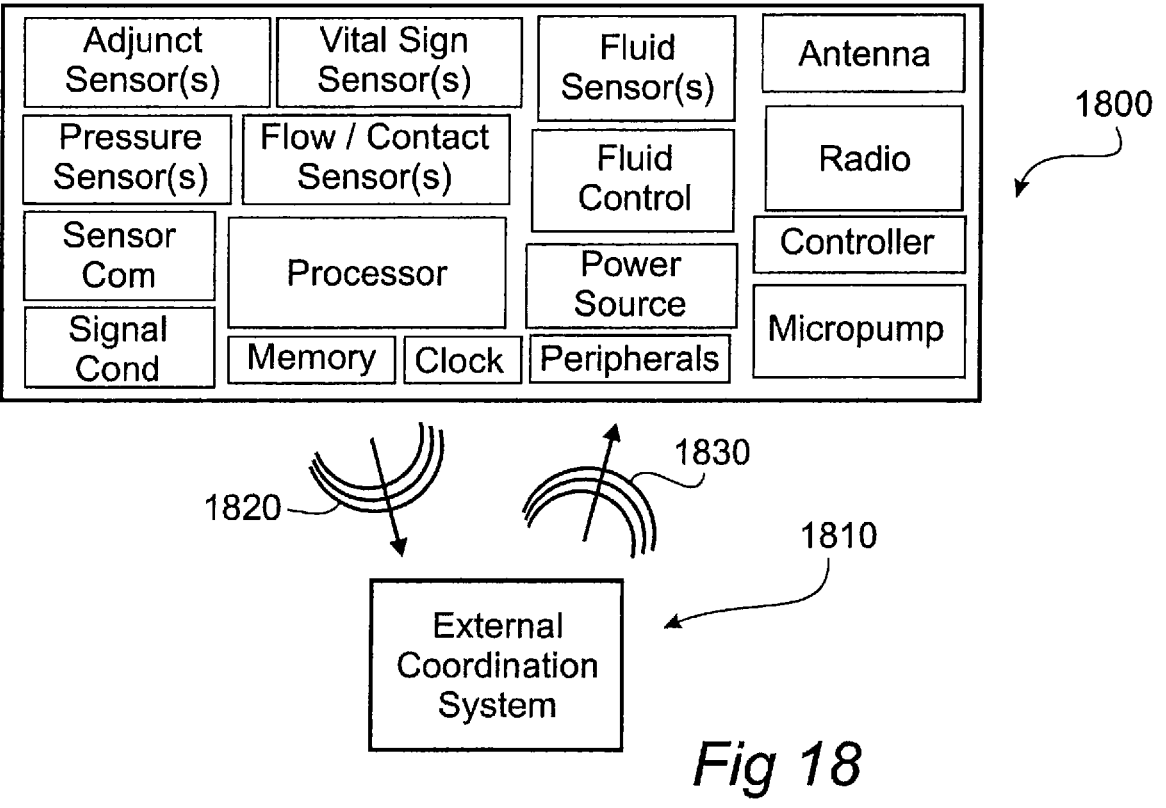

FIG. 18 shows a schematic of aspects of a control unit 1800 in accordance with the present disclosure including one or more adjunct sensors, one or more vital sign sensors, one or more fluid sensors, one or more pressure sensors, one or more flow/contact sensors, a sensor communication unit, a signal conditioning unit, a fluid control system, a micropump, a power source, a processor, a memory element, a clock source, one or more peripherals, a controller (e.g. to control the micropump), a radio and an antenna.

The control unit 1800 is configured to operably draw a breath gas sample from a subject in order to generate one or more signals related to one or more metabolic and/or cardiopulmonary parameters. The control unit 1800 is configured to communicate one or more signals 1820, 1830 with an external coordination system 1810 (alternatively a user device).

Figure 19:
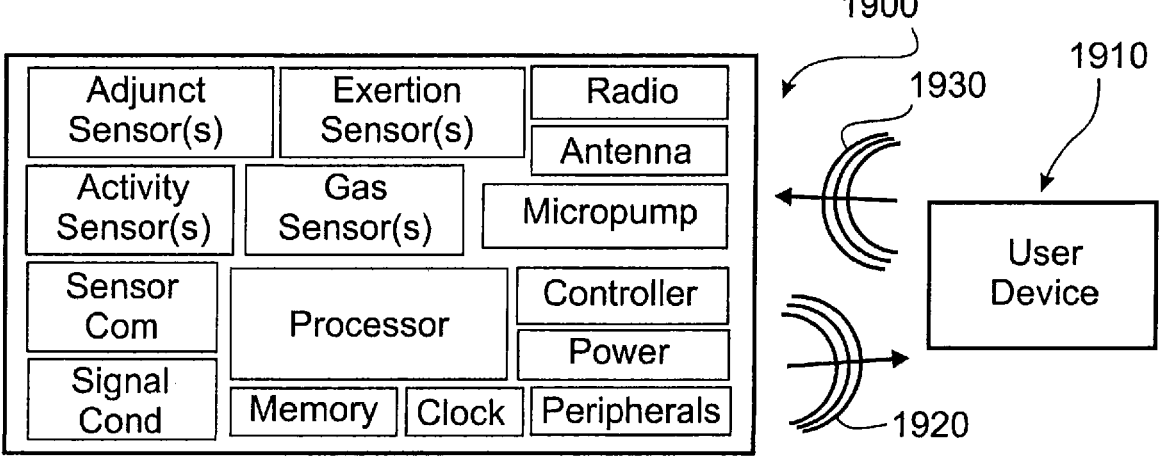

FIG. 19 shows a schematic of aspects of a control unit 1900 in accordance with the present disclosure including one or more adjunct sensors, one or more exertion sensors, one or more activity sensors, one or more gas sensors, a sensor communication unit, a signal conditioning unit, a micropump, a processor, a memory element, a clock, a power source, one or more peripherals, a radio and an antenna.

The control unit 1900 may be configured to operably draw a breath gas sample from a subject in order to generate one or more signals related to one or more metabolic and/or cardiopulmonary parameters. The control unit 1900 may be configured to communicate one or more signals 1920, 1930 with a user device 1910 (alternatively a communication system, an external coordination system, etc.).

Figure 20A:
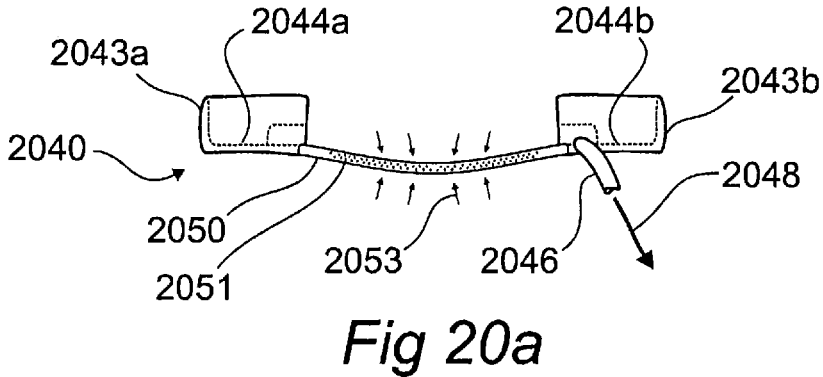
FIGS. 20*a-c*—Show examples of an aspect of a sampling module in accordance with the present disclosure.
Figure 20B:
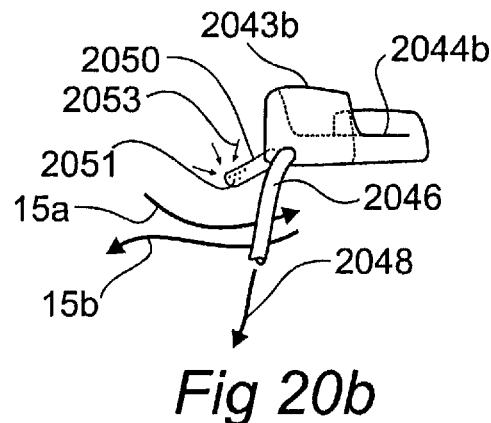
Figure 20C:
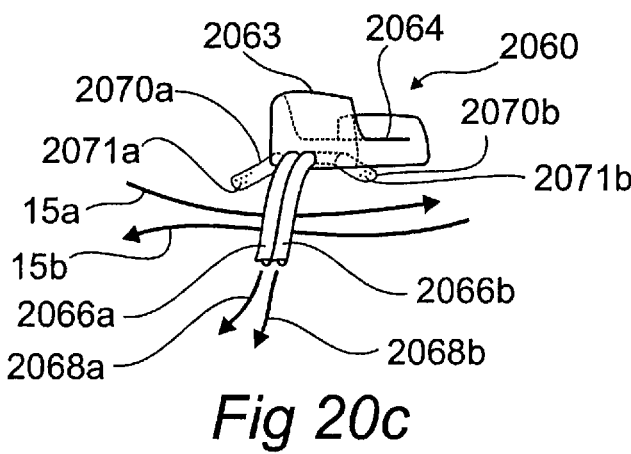

FIGS. 20a-c show aspects of a sampling module in accordance with the present disclosure. FIGS. 20a-b show a front facing view (FIG. 20a) and a side facing view (FIG. 20b) of an intra-oral interfacing component 2040 included in a sampling module in accordance with the present disclosure. The interfacing component 2040 includes one or more mounting blocks 2043a,b with one or more troughs 2044a,b shaped so as to retain the interfacing component 2040 against the teeth of the subject when fitted. The mounting blocks 2043a,b and/or troughs 2044a,b may be formed from a remoldable material (e.g. formed from a remoldable thermoplastic elastomers, SEBS, styrenic block copolymers, polyolefin blends, elastomeric alloys (TPE-v or TPV), thermoplastic polyurethanes, thermoplastic copolyester and thermoplastic polyamides as provided under the trade names Arntitel (DSM), Engage (Dow chemical), Hytrel (Du Pont), or Kraton).

The interfacing component 2040 may include a bridge 2050 with a plurality of microholes 2051 in fluid communication with a tubule 2046 for drawing a breath gas sample 2048 from the breath stream 15a,b of the subject. The bridge 2050 may be hollow or include a channel for interfacing the microholes 2051 with a lumen within the tubule 2046. The bridge 2050 may be at least partially formed and/or coated from a hydrophobic material (e.g. a polymer, polytetrafluoroethylene (PTFE), etc.) so as to substantially minimize fluid ingress into the micoholes 2051 during use. The bridge 2050 may be at least somewhat moldable so as to help with achieving a snug fit in the oral cavity of the subject during a fitting procedure.

The plurality of microholes 2051 may be configured to effectively break up the breath stream 15a,b into a plurality of jets 2053.

FIG. 20c shows aspects of an interfacing component 2060 configured to monitor one or more flow parameters, optionally in combination with one or more breath gas samples, from the breath stream 15a,b during use. The interfacing component 2060 includes one or more mounting blocks 2063, with associated troughs 2064 for interfacing with the teeth of a subject. The interfacing component 2060 includes a plurality of bridges 2070a,b, each with associated microholes 2071a,b in fluid communication with a lumen within one or more tubules 2066a,b to draw one or more breath gas samples 2068a,b. The microholes 2071a,b may be provided in fluid communication with a transducer for generating an absolute, gauge and/or differential pressure signal representative of at least a portion of a flow parameter within the breath stream 15a,b.

The bridges 2070a,b may be at least partially formed and/or coated from a hydrophobic material (e.g. a polymer, polytetrafluoroethylene (PTFE), etc.) so as to substantially minimize fluid ingress into the microholes 2071a,b during use. The bridges 2070a,b may be at moldable so as to help with achieving a snug fit in the oral cavity of the subject during a fitting procedure.

Figure 21:
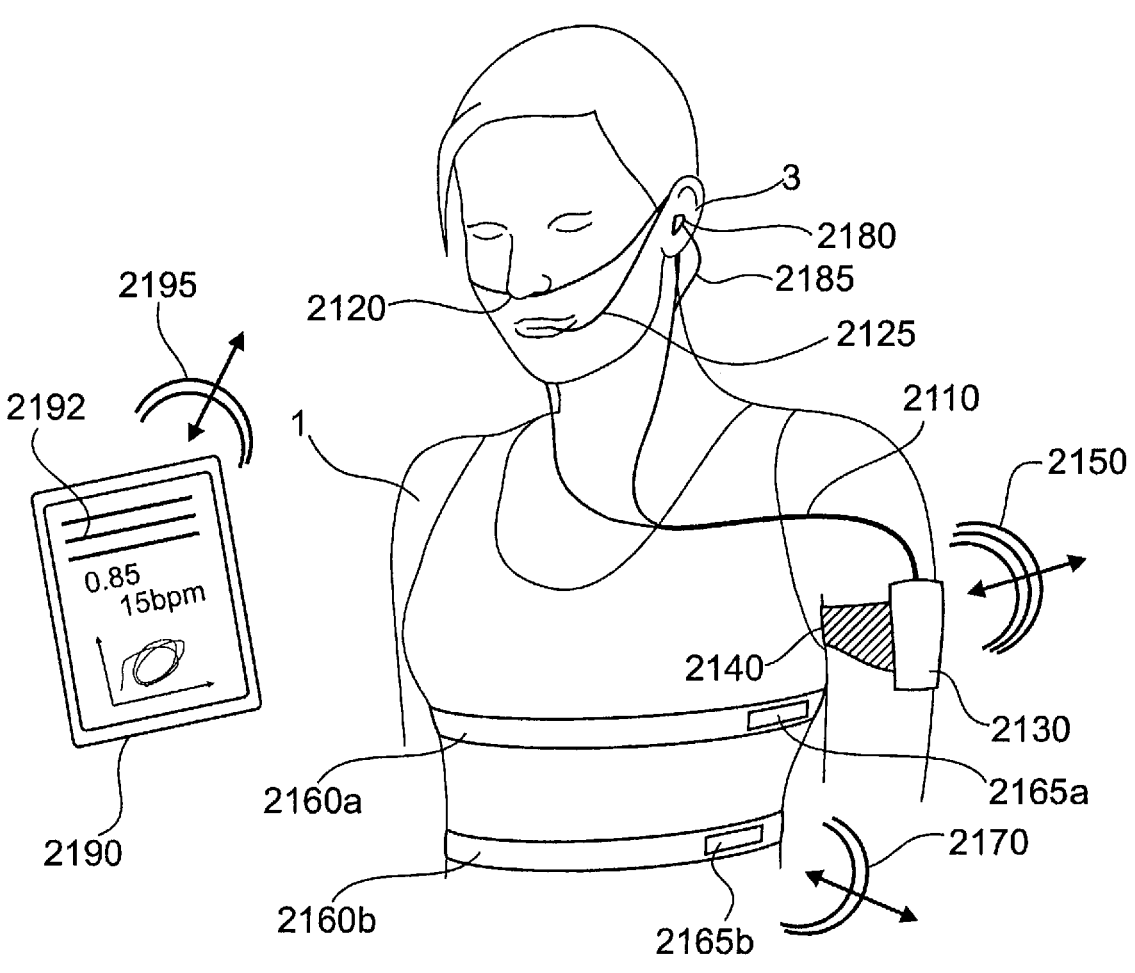
FIG. 21—Shows an example of a data system in accordance with the present disclosure.

FIG. 21 shows a data system including a user device 2190 (e.g. a tablet computer, a smartphone, etc.), a wearable system and a wireless respiratory volume sensor each in accordance with the present disclosure. The user device 2190 may be configured to communicate signals 2195, 2150, 2170 with the wearable system and/or the respiratory volume sensor. The respiratory volume sensor may include a plurality of bands 2160a,b, each band including a circumferential sensor, and a control circuit 2165a,b configured to interface with the circumferential sensor and communicate associated signals 2170 to the wearable system or the user device 2190. The wearable system may include a control unit 2130 attached to the subject 1 via an armband 2140 (in the example shown, alternatively mountable on the belt, neck, headband, ear clip, integrated into clothing, a wristband, or the like). The wearable system may include a sampling module 2110 connected to the control unit 2130.

The sampling module 2110 includes a nasal interfacing component 2120, an oral interfacing component 2125, an ear bud 2180 (e.g. optionally including an ear bud speaker, an spO2 sensor, etc.) place-able within the ear 3 of the subject 1. The ear bud 2180 is attached to the elongate portion of the sampling module 2110 via a tether element 2185, which may include electrical wiring or optical fibers for communicating one or more signals with the ear 3 of the subject 1 and the control unit 2150.

The user device 2190 may display data 2192 for a user (e.g. the subject, a coach, a clinician, a technician, a doctor, etc.) relating to the monitoring process. The user device 2190 may aggregate and display data 2192 from a plurality of subjects, each wearing an associated wearable system.

It will be appreciated that additional advantages and modifications will readily occur to those skilled in the art. Therefore, the disclosures presented herein and broader aspects thereof are not limited to the specific details and representative embodiments shown and described herein. Accordingly, many modifications, equivalents, and improvements may be included without departing from the spirit or scope of the general inventive concept as defined by the appended claims and their equivalents.

What is claimed is:

1. A system, comprising:
   a control unit configured to be worn by a subject, the control unit comprising:
   one or more processors operatively coupled to a memory;
   a wireless transceiver; and
   a power supply for powering the one or more processors;
   a computing device independent of the control unit, the computing device comprising:
   one or more processors operatively coupled to a memory;
   a wireless transceiver in communication with the wireless transceiver of the control unit; and
   a display; and
   at least one primary sensor mountable relative to the subject, the at least one primary sensor being configured to generate one or more primary signals representative of a respiratory volume of the subject, and to communicate the one or more primary signals to one of the control unit and the computing device;
   one or more secondary sensors mountable relative to the subject, a given sensor of the one or more secondary sensors being configured to generate one or more secondary signals distinct from the one or more primary signals and representative of a flow velocity of a respiratory stream of the subject, and to communicate the one or more secondary signals to one of the control unit and the computing device; and
   a sampling module including an interfacing component configured for fluid coupling to the respiratory stream of the subject, the interfacing component comprising a manifold comprising a flow channel configured for directing a flow of the respiratory stream of the subject, the flow channel comprising a support structure comprising a first portion extending across the flow channel in a first direction and a second portion extending across the flow channel in a second direction different than the first direction, wherein the at least one secondary sensor is mounted on the first portion of the support structure and one or more sample ports are mounted on the second portion of the support structure.

2. The system of claim 1, wherein the one or more primary signals are one or more volumetric signals.

3. The system of claim 2, wherein the one or more volumetric signals are communicated to the control unit.

4. The system of claim 3, wherein the one or more processors of the control unit are configured to generate one or more signals corresponding to the one or more volumetric signals, and wherein the one or more corresponding signals are transmitted to the wireless transceiver of the computing device.

5. The system of claim 4, wherein the one or more processors of the computing device are configured to cause the display of data, associated with the one or more signals corresponding to the one or more volumetric signals, on the display.

6. The system of claim 2, further comprising a plurality of respiratory volume sensors, each respiratory volume sensor mounted to an attachment member, each attachment member being configured for securement relative to the chest or abdomen of the subject.

7. The system of claim 1, wherein a second given sensor of the one or more secondary sensors comprises one of a heart-rate sensor, an EKG sensor, an EMG sensor, a galvanic skin response sensor, a pulse oximeter, a core temperature sensor and a cardiac output sensor.

8. The system of claim 1, further comprising an ear bud mountable relative to an ear of the subject, the ear bud comprising at least one of a speaker and a bud sensor in communication with the control unit.

9. The system of claim 1, wherein the interfacing component is configured for at least partial insertion in a nasal cavity or an oral cavity of the subject.

10. The system of claim 9, further comprising one or more sensory elements coupled to the interfacing component, the one or more sensory elements being configured to measure one or more physiological or dimensional parameters of the nasal cavity or the oral cavity of the subject.

11. The system of claim 9, wherein the given sensor of the one or more secondary sensors includes at least one sensing membrane disposed within the interfacing component, the at least one sensing membrane being configured to generate a response dependent upon one or more properties of the respiratory stream.

12. The system of claim 11, wherein the at least one sensing membrane is configured to detect a presence of an analyte in the respiratory stream.

13. The system of claim 12, further comprising a detector in communication with the at least one sensing membrane, the detector configured to generate one or more analyte signals related to the analyte.

14. The system of claim 13, wherein the one or more analyte signals is transmitted to the control unit and wherein the control unit is configured to generate one or more signals corresponding to the one or more analyte signals, and wherein the one or more corresponding signals are transmitted to the wireless transceiver of the computing device.

15. The system of claim 14, wherein the one or more processors of the computing device are configured to cause the display of data, associated with the one or more signals corresponding to the one or more analyte signals, on the display.

16. The system of claim 1, wherein the control unit further comprises one or more gas sensors arranged in operable fluid communication with the respiratory stream, and configured to analyze at least one of metabolic and physiological parameters of the respiratory stream.

17. The system of claim 1, wherein the flow channel has a changing profile configured to slow or accelerate flow through the manifold.

18. The system of claim 1, wherein at least one of the first portion and the second portion of the support structure provides a partial obstruction of flow through the flow channel.

19. The system of claim 18, wherein the one or more sample ports are configured to extract a breath gas sample from the respiratory stream of the subject.

20. The system of claim 19 wherein at least one of the one or more sample ports is in fluid communication with one or more pressure transducers configured to capture a differential pressure reading relating to one or more characteristics of the respiratory stream of the subject.

\* \* \* \* \*